(12) United States Patent
Ron Edoute et al.

(10) Patent No.: US 8,979,727 B2
(45) Date of Patent: Mar. 17, 2015

(54) ESTHETIC APPARATUS USEFUL FOR INCREASING SKIN REJUVENATION AND METHODS THEREOF

(71) Applicant: Venus Concept Ltd, Karmiel (IL)

(72) Inventors: Oded Ron Edoute, Tel Aviv (IL); Orit Ron Edoute, Tel Aviv (IL); Itzhak Kremin, Givatayim (IL); Vadim Polyakov, Petach Tikva (IL)

(73) Assignee: Venus Concept Ltd., Karmiel (IL)

( * ) Notice: Subject to any disclaimer, the term of this patent is extended or adjusted under 35 U.S.C. 154(b) by 0 days.

(21) Appl. No.: 13/954,320

(22) Filed: Jul. 30, 2013

(65) Prior Publication Data

US 2013/0317282 A1 Nov. 28, 2013

Related U.S. Application Data

(62) Division of application No. 13/001,834, filed as application No. PCT/IL2009/000644 on Jun. 29, 2009.

(60) Provisional application No. 61/076,652, filed on Jun. 29, 2008, provisional application No. 61/112,783, filed on Nov. 10, 2008.

(51) Int. Cl.
*A61F 7/00* (2006.01)
*A61N 7/02* (2006.01)
(Continued)

(52) U.S. Cl.
CPC . *A61F 7/00* (2013.01); *A61N 1/328* (2013.01); *A61N 1/403* (2013.01); *A61N 2/002* (2013.01);
(Continued)

(58) Field of Classification Search
CPC ........... A61N 2/02; A61N 1/40; A61N 1/326; A61N 2/008; A61N 1/403; A61N 7/02; A61N 2/002; A61N 1/328; A61B 18/14; A61B 2018/00642; A61B 2018/00875; A61H 2201/10; A61H 39/002
USPC .............. 600/9, 10, 13, 14, 15; 128/897–899; 607/1, 2, 3, 103, 115
See application file for complete search history.

(56) References Cited

U.S. PATENT DOCUMENTS 4,140,130 A 2/1979 Storm, III
5,778,894 A * 7/1998 Dorogi et al. ................. 128/898
(Continued)

FOREIGN PATENT DOCUMENTS

DE 304 587 A 3/1930
DE 33 40 974 A1 5/1985
(Continued)

OTHER PUBLICATIONS

Zelickson et al., "Histological and ultrastructural evaluation of the effects of a radiofrequency-based nonablative dermal remodeling device: a pilot study."Arch Dermatol, Feb. 2004, 140 (2); pp. 204-209. Department of Dermatology, University of Minnesota, Minneapolis, MN, USA.
(Continued)

*Primary Examiner* — Christine Matthews
*Assistant Examiner* — Joshua D Lannu
(74) *Attorney, Agent, or Firm* — The Law Office of Michael E. Kondoudis

(57) ABSTRACT

Systems and methods for increasing skin rejuvenation of a region of a patient's skin. The system includes: a pulsed electromagnetic field (PEMF) frequency generator that emits electromagnetic pulses to the region of the patient's skin; and a deep tissue diathermy device that applies heat to the region of the patient's skin up to temperature T. The system simultaneously applies the heat and the PEMF to the region of a patient's skin.

11 Claims, 17 Drawing Sheets

(51) Int. Cl.
| | | |
|---|---|---|
| *A61N 1/32* | (2006.01) | |
| *A61N 1/40* | (2006.01) | |
| *A61N 2/00* | (2006.01) | |
| *A61B 18/20* | (2006.01) | |
| *A61B 18/00* | (2006.01) | |
| *A61N 2/02* | (2006.01) | |

(52) U.S. Cl.
CPC ..... *A61N 7/02* (2013.01); *A61N 2/004* (2013.01); *A61B 18/203* (2013.01); *A61B 2018/00452* (2013.01); *A61N 2/02* (2013.01)
USPC ............. 600/14; 601/3; 607/100; 607/101; 607/98

(56) References Cited

U.S. PATENT DOCUMENTS

| | | | |
|---|---|---|---|
| 6,453,202 B1* | 9/2002 | Knowlton | 607/102 |
| 2004/0034346 A1 | 2/2004 | Stern | |
| 2005/0182462 A1 | 8/2005 | Chornenky et al. | |
| 2005/0187599 A1 | 8/2005 | Sharkey | |
| 2006/0293719 A1 | 12/2006 | Naghavi | |
| 2008/0249350 A1* | 10/2008 | Marchitto et al. | 600/10 |

FOREIGN PATENT DOCUMENTS

| | | |
|---|---|---|
| DE | 38 25 165 A1 | 1/1990 |
| GB | 2 188 238 A | 9/1987 |
| WO | 93 12835 A | 7/1993 |
| WO | 9805380 | 5/1998 |
| WO | 00 53113 A | 9/2000 |
| WO | 2008064272 | 5/2008 |
| WO | 2009 047628 A | 4/2009 |

OTHER PUBLICATIONS

Rosch et al., "Bioelectromagnetic Medicine", Apr. 2004, pp. 251-264. Marcel Dekker, New York, NY, USA.
Ahmadian et al., "Effects of extremely-low frequency pulsed electromagnetic fields on collagen synthesis in rat skin", Biotechnology and Applied Biochemistry, Feb. 2006, vol. 43, Issue 2, pp. 71-75, 2006 International Union of Biochemistry and Molecular Biology.
Tepper et al., "Electromagnetic fields increase in vitro and in vivo angiogenesis through endothelial release of FGF-2", FASEB Journal, Aug. 2004, 18(11), pp. 1231-1233, Epub Jun. 18, 2004, The Laboratory of Microvascular Research and Vascular Tissue Engineering, New York University School of Medicine, New York, NY, USA.
International Search Report and Written Opinion received in PCT Appln. No. PCT/IL2009/000644 mailed Mar. 23, 2010.

* cited by examiner

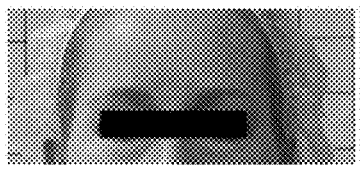 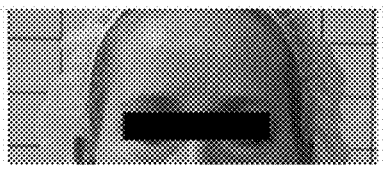 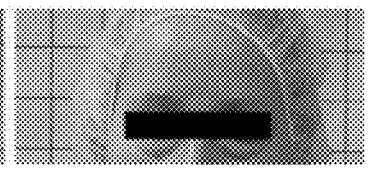
FIG.13E  FIG.13C  FIG.13A
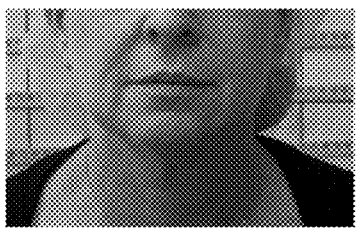 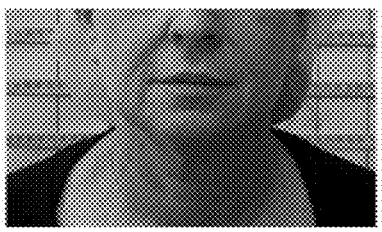 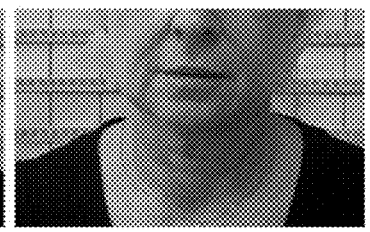
FIG.13F  FIG.13D  FIG.13B

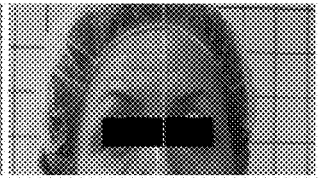
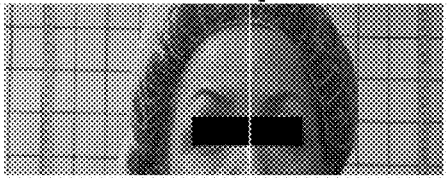
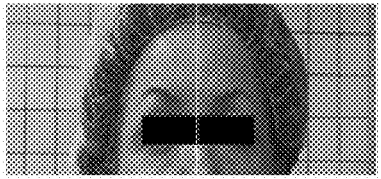
FIG.16E                    FIG.16C                    FIG.16A
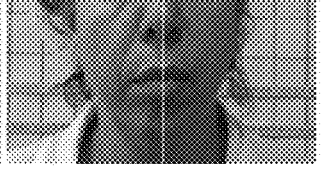
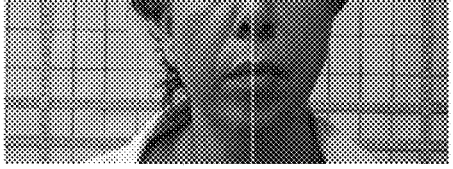
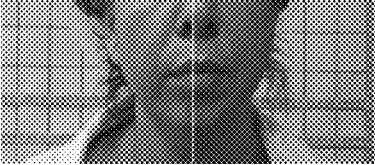
FIG.16F                    FIG.16D                    FIG.16B

ESTHETIC APPARATUS USEFUL FOR INCREASING SKIN REJUVENATION AND METHODS THEREOF

FIELD OF THE INVENTION

This invention generally relates to an esthetic device used to improve skin viability and skin rejuvenation, and a method of using the device.

BACKGROUND OF THE INVENTION

Improving the appearance of the skin has been the goal of many esthetic products and procedures for many years, since a tight skin, without wrinkles or cellulite, has a younger and more appealing appearance. Apart from age related changes, the skin also suffers from exposure to chemical and physical injuries, such as tobacco, cosmetics, esthetics and radiation from the sun and other sources. Those factors contribute to the decrease in collagen production, to reduced elasticity, and the appearance of wrinkles.

A few main approaches to tightening of the skin are common practice today. The surgical approach carries disadvantages related to the anesthesia, the surgical complications, and the healing process, which may cause scars. The chemical peel approach usually involves injury to the outermost layer of the skin—the epidermis—which may cause discoloration. Since collagen fibers are found in the dermis—the subcutaneous layer of the skin, and since heat was shown to contract these fibers and generate their production [Zelickson B D, Kist D, Bernstein E, Brown D B, Ksenzenko S, Burns J, Kilmer S, Mehregan D, Pope K. Histological and ultrastructural evaluation of the effects of a radiofrequency-based nonablative dermal remodeling device: a pilot study. Arch Dermatol. 2004 February; 140(2):204-9], methods of differentially heating the dermis (deep tissue diathermy) have recently arisen.

A unique method of treating the dermis is called Pulsed Electromagnetic Fields (PEMF) therapy. This method usually employs electromagnetic radiation of different frequencies—ranging from static magnetic fields, through extremely low frequencies (ELF) to higher radiofrequencies (RF)—administered in pulses.

PEMF works in few ways. Due to the radiation absorbed in the tissue, it can be heated to various temperatures, depending on the power applied, the frequency transmitted, and more importantly the tissue characteristics. Eventually, the tissue can be warmed to denaturation temperatures, which cause coagulation necrosis and tissue damage. It can also be heated to lower temperatures, which proved to result in the aforementioned contraction of collagen fibers.

Another modus operandi involves non thermal effects. These rely on specific tissue components and their reaction to the applied radiation characteristics. These effects might be due to large charged molecules and their reaction to various frequencies and frequency harmonies, charged small ions in the cell membranes affecting the cells function and reactions to hormones and chemical signals, charged small ions in the extracellular space and other poorly understood mechanisms.

Furthermore, applying the radiation in pulses was also found to have non thermal effects. Yet more, only a specific combination of frequency, duty cycle and transmitted power achieve a specific tissue response. Recent scientific research has confronted these challenges and found the PEMF characteristics needed for the desired biophysical response.

It is now commonly accepted that weak electromagnetic fields (EMF) administered in pulses are capable of initiating various healing processes in fractures, multiple sclerosis and Parkinson's disease, and even delivering pain relief; however it seems that most of the conditions that seem most likely to respond to PEMF are musculoskeletal. The FDA has allowed the use of pulsed radiofrequency electromagnetic field for treatment of pain and edema in superficial soft tissues two decades ago. [Rosch, P. J., Markov, M. S., eds. Bioelectromagnetic Medicine, Marcel Dekker, NY, 251-264].

The use of PEMF can also be recruited for cosmetic purposes as described above. Several studies have addressed the effect of PEMF on dermal components. For example, in vivo trials showed that pulsed electromagnetic field of certain field intensities and frequencies increased epidermal collagen synthesis [Ahmadian S, Zarchi S R, Bolouri B. Effects of extremely-low-frequency pulsed electromagnetic fields on collagen synthesis in rat skin. Biotechnol Appl Biochem. 2006 February; 43(Pt 2):71-5]. This new formed collagen increases skin elasticity and rejuvenates its appearance.

In vitro trials showed that PEMF increased the degree of endothelial cell tubulization and proliferation, and augmented angiogenesis primarily by stimulating endothelial release of FGF-2, inducing paracrine and autocrine changes in the surrounding tissue [Tepper O M et al. Electromagnetic fields increase in vitro and in vivo angiogenesis through endothelial release of FGF-2. FASEB J. 2004 August; 18(11): 1231-3. Epub 2004 Jun 18]. Angiogenesis, the sprouting of new blood vessels, increases blood flow to the tissue, which in turn increases oxygen and nutritional substances delivery to the tissue. This effect is most beneficial for an injured tissue, promoting rapid and improved healing. The growth factor released further enhances the healing process, both in quality and time of improvement.

The scientific evidence of the effect of PEMF on tissues was utilized in various applications. For example, US20050182462A1 discloses healthy deep tissue heating using PEMF for the purpose of causing contraction and tightening of the skin.

PEMF has also been used to improve skin wound healing. For example, WO08064272 discloses a method of treating a severe diabetic ulcer using PEMF. The patent also discloses the addition of intermittent compression therapy (ICT) and the use of low intensity ultrasound (up to 50 W/cm$^2$), the latter aimed at inhibiting microbial growth.

Other methods of heating the dermis used non pulsating RF radiation, applied by antenna or electrodes. For example, WO98005380 discloses a method of tightening skin using an RF electromagnetic energy delivery device.

Improving the results of skin tightening based on dermis diathermy is still a long felt need, both for esthetic and therapeutic purposes.

SUMMARY OF THE INVENTION

It is one object of the present invention to provide a system (10) adapted to increase skin rejuvenation of a region of a patient's skin, said system comprising
  a. a pulsed electromagnetic field (PEMF) frequency generator (2) for constantly providing electromagnetic pulses to said region of a patient's skin; and,
  b. a deep tissue diathermy device (4) for constantly applying heat to said region of a patient's skin up to temperature T;
said system (10) is adapted for simultaneously applying heat and PEMF to said region of a patient's skin; wherein application of said system increases said skin rejuvenation such that said skin rejuvenation increase (SRI) is greater than the sum of said SRI provided by electromagnetic pulses increase and said SRI provided by said deep tissue diathermy device increase.

It is another object of the present invention to provide the system as defined above, wherein said electromagnetic pulse is a triangular shaped at frequency of 25 Hz and intensity of 20 Gauss.

It is another object of the present invention to provide the system as defined above, wherein said electromagnetic pulse is square shaped at a frequency of 16 Hz, duration of about 5 milliseconds and intensity of 12 Gauss.

It is another object of the present invention to provide the system as defined above, wherein said deep tissue diathermy device (4) is selected from any device emitting RF radiation or any means adapted for producing electrical current absorbed by subcutaneous tissue.

It is another object of the present invention to provide the system as defined above, wherein said deep tissue diathermy device (4) additionally comprises:
  a. at least one electrical output device adapted to generate RF electromagnetic energy;
  b. at least two electrodes electrically coupled to said electrical output device and placed on said skin region, wherein all said electrodes are adapted to simultaneously apply said RF energy to said skin region.

It is another object of the present invention to provide the system as defined above, wherein said deep tissue diathermy device (4) additionally comprises:
  a. at least one electrical output device adapted to generate electrical current;
  b. at least two electrodes electrically coupled to said electrical output device and placed on said skin region, wherein all said electrodes are adapted to simultaneously apply said electrical current to said skin region.

It is another object of the present invention to provide the system as defined above, wherein said system reduces side effects and/or harmful effects of said electromagnetic pulses and/or said deep tissue diathermy such that said reduction of said side effects and/or said harmful effects is greater than the sum of said reduction of said electromagnetic pulses and/or said reduction of said deep tissue diathermy.

It is another object of the present invention to provide the system as defined above, wherein said system additionally comprising a control system (6) adapted to regulate said electromagnetic pulses and/or said electromagnetic pulses.

It is another object of the present invention to provide the system as defined above, wherein said pulsed electromagnetic frequency generator is adapted to provide a dynamic magnetic field such that said electromagnetic pulses vary with time.

It is another object of the present invention to provide the system as defined above, wherein the shape of said electromagnetic pulse is selected in a non-limiting manner from a group consisting of square wave, a sine wave, a triangular wave, sawtooth wave, ramp waves, spiked wave or any other mathematical combination.

It is another object of the present invention to provide the system as defined above, wherein the magnetic field intensity B of each pulse applied by said pulsed electromagnetic frequency generator (2) ranges between about 0 and about 3 Tesla.

It is another object of the present invention to provide the system as defined above, wherein the duration of each pulse applied by said pulsed electromagnetic frequency generator (2) ranges between about 3 and about 1000 milliseconds.

It is another object of the present invention to provide the system as defined above, wherein the frequency F applied by the pulses of said pulsed electromagnetic frequency generator (2) ranges between about 1 Hz and about 1M Hz.

It is another object of the present invention to provide the system as defined above, wherein the energy E applied by the pulses of said pulsed electromagnetic frequency generator (2) ranges between about 1 and about 150 watts per pulse.

It is another object of the present invention to provide the system as defined above, wherein said deep tissue diathermy device (4) is selected in a non-limiting manner from a group consisting of an ultrasonic diathermy, an optical device, electromagnetic induction, sound waves emitting instrument, direct heat applying instrument, or from any other means of heating subcutaneous tissue to temperature T.

It is another object of the present invention to provide the system as defined above, wherein said optical device is adapted to emit light in wavelengths absorbed by subcutaneous tissue such that said subcutaneous tissue is heated.

It is another object of the present invention to provide the system as defined above, wherein said sound waves emitting instrument is adapted to emit sound waves absorbed by the subcutaneous tissue such that said subcutaneous tissue is heated.

It is another object of the present invention to provide the system as defined above, wherein said temperature T is higher than about 30 and lower than about 80 degrees.

It is another object of the present invention to provide the system as defined above, wherein said power supply and control system (6) monitors physical tissue parameters and changes applied heat and electromagnetic pulses accordingly.

It is another object of the present invention to provide the system as defined above, wherein said power supply and control system (6) additionally comprising:
  a. processing means, adapted to store in a communicable database predetermined parameters defining (i) safe treatment parameters and (ii) unsafe treatment parameters; said parameters are selected from a group consisting of time t of said treatment, temperature T of said tissue, ratio t/T, Frequency F, power P, energy E applied by the pulses of said pulsed electromagnetic frequency generator, depth D of said treated tissue, magnetic field intensity B, tissue impedance, specific absorption rate (SAR), treatment depth, superficial muscle contractions or a combination thereof;
  b. sensing means; adapted to sense electromagnetic radiation and heat radiation parameters selected from a group consisting of time t of time t of said treatment, temperature T of said tissue, ratio t/T, Frequency F, power P, Intensity I of said ultrasound irradiation, energy E applied by the pulses of said pulsed electromagnetic frequency generator, depth D of said treated tissue, magnetic field intensity B, tissue impedance, specific absorption rate (SAR), treatment depth, superficial muscle contractions or a combination thereof;
  c. regulating means, adapted to allow said electromagnetic radiation and heat radiation if said parameters are within said safe treatment parameters and to stop the electromagnetic radiation if the radiation parameters are in said unsafe treatment parameters.

It is another object of the present invention to provide the system as defined above, wherein said power supply and control system (6) includes a mechanism for skin cooling.

It is another object of the present invention to provide the system as defined above, wherein said system (10) is encased in at least one platform.

It is another object of the present invention to provide the system as defined above, wherein said pulsed electromagnetic frequency generator (2) and said deep tissue diathermy device (4) have more than one applicator to treat more than one body part simultaneously.

It is another object of the present invention to provide the system as defined above, wherein said pulsed electromagnetic frequency generator (2) has electrostatic shielding.

It is another object of the present invention to provide the system as defined above, especially adapted to increase skin rejuvenation in the immediate (short) range.

It is another object of the present invention to provide the system as defined above, especially adapted to increase skin rejuvenation in the intermediate range.

It is another object of the present invention to provide the system as defined above, especially adapted to increase skin rejuvenation in the long range.

It is another object of the present invention to provide the system as defined above, wherein said system is especially adapted to operate according to IEC selected from a group consisting of IEC 60601-2-35, IEC 60601-2-33, IEC 60601-2-29, IEC 60601-2-9, IEC 60601-2-5, IEC 60601-2-3, IEC 60601-1-8, IEC 60601-1-6, IEC 60601-1-4, IEC 60601-1-3, IEC 60601-1-2, IEC 60601-1-1 or any combination thereof.

It is another object of the present invention to provide a method (400) of increasing skin rejuvenation of a region of a patient's skin. The method comprises steps selected inter alia from:
 a. obtaining (i) pulsed electromagnetic frequency generator; and, (ii) a deep tissue diathermy device;
 b. applying heat to a subcutaneous tissue within said region up to temperature T; and,
 c. applying pulses of electromagnetic field to said region;
wherein said increasing of said skin rejuvenation is greater than the sum of said applying heat to a subcutaneous tissue within said region increase and said applying pulses electromagnetic therapy to said region increase.

It is another object of the present invention to provide a method (410) of increasing skin rejuvenation of a region of a patient's skin. The method comprises steps selected inter alia from:
 a. obtaining (i) pulsed electromagnetic frequency generator; and, (ii) a deep tissue diathermy device;
 b. applying pulses of electromagnetic field to said region; and,
 c. applying heat to a subcutaneous tissue within said region up to temperature T;
wherein said increasing of said skin rejuvenation is greater than the sum of said applying heat to a subcutaneous tissue within said region and said applying pulses electromagnetic therapy to said region It is another object of the present invention to provide a method (420) of increasing skin rejuvenation of a region of a patient's skin. The method comprises steps selected inter alia from:
 a. obtaining (i) pulsed electromagnetic frequency generator; and, (ii) a deep tissue diathermy device;
 b. applying heat to a subcutaneous tissue within said region up to temperature T; whilst simultaneously applying pulses of electromagnetic field to said region;
wherein said increasing of said skin rejuvenation is greater than the sum of said applying heat to a subcutaneous tissue within said region and said applying pulses electromagnetic therapy to said region.

It is another object of the present invention to provide the methods as defined above, wherein said system reduces side effects and/or harmful effects of said electromagnetic pulses and/or said deep tissue diathermy such that said reduction of said side effects and/or said harmful effects is greater than the sum of said reduction of said electromagnetic pulses and/or said reduction of said deep tissue diathermy.

It is another object of the present invention to provide the methods as defined above, additionally comprising step of monitoring and/or controlling said steps of applying heat to a subcutaneous tissue within said region and/or said step of applying pulsed electromagnetic therapy to said region.

It is another object of the present invention to provide the methods as defined above, additionally comprising step of applying a dynamic magnetic field onto said region.

It is another object of the present invention to provide the methods as defined above, additionally comprising steps of
 a. storing in a communicable database predetermined parameters defining (i) safe treatment parameters and (ii) unsafe treatment parameters; said parameters are selected from a group consisting of time t of said treatment, temperature T of said tissue, ratio t/T, Frequency F, power P, energy E applied by the pulses of said pulsed electromagnetic frequency generator, depth D of said treated tissue, magnetic field intensity B, tissue impedance, specific absorption rate (SAR), treatment depth, superficial muscle contractions or a combination thereof;
 b. sensing electromagnetic radiation and heat radiation parameters selected from a group consisting of time t of said treatment, temperature T of said tissue, ratio t/T, Frequency F, power P, Intensity I of said ultrasound irradiation, energy E applied by the pulses of said pulsed electromagnetic frequency generator, depth D of said treated tissue, magnetic field intensity B, tissue impedance, specific absorption rate (SAR), treatment depth, superficial muscle contractions or a combination thereof;
 c. allowing said electromagnetic radiation and said heat radiation if parameters within said safe treatment parameters and to stop the electromagnetic radiation if the radiation parameters are in said unsafe treatment parameters.

It is another object of the present invention to provide the methods as defined above, additionally comprising step of selecting the shape of said electromagnetic pulse is selected in a non-limiting manner from a group consisting of square wave, a sine wave, a triangular wave, sawtooth wave, ramp waves, spiked wave or any other mathematical combination.

It is another object of the present invention to provide the methods as defined above, additionally comprising step of applying a triangular shaped electromagnetic pulse at frequency of 25 Hz and intensity of 20 Gauss.

It is another object of the present invention to provide the methods as defined above, additionally comprising step of applying a square shaped electromagnetic pulse at a frequency of 16 Hz, duration of about 5 milliseconds and intensity of 12 Gauss.

It is another object of the present invention to provide the methods as defined above, additionally comprising step of selecting said deep tissue diathermy device (4) from any device emitting RF radiation or any means adapted for producing electrical current absorbed by subcutaneous tissue.

It is another object of the present invention to provide the methods as defined above, wherein said step of applying heat to a subcutaneous tissue additionally comprising steps of
 a. obtaining at least one electrical output device adapted to generate RF electromagnetic energy;
 b. electrically coupling at least two electrodes to said electrical output device;
 c. placing said at least two electrodes on said skin region; and, d. simultaneously applying via all said electrodes said RF energy to said skin region.

It is another object of the present invention to provide the methods as defined above, wherein said step of applying heat to a subcutaneous tissue additionally comprising steps of
- a. obtaining at least one at least one electrical output device adapted to generate electrical current;
- a. electrically coupling at least two electrodes to said electrical output device;
- b. placing said at least two electrodes on said skin region; and,
- c. simultaneously applying via all said electrodes said electrical current to said skin region.

It is another object of the present invention to provide the methods as defined above, additionally comprising step of selecting said temperature T from a region of about 30 to about 80 degrees.

It is another object of the present invention to provide the methods as defined above, additionally comprising step of selecting the duration of each pulse applied by said pulsed electromagnetic frequency generator (2) to be higher than about 3 and lower than about 1000 milliseconds.

It is another object of the present invention to provide the methods as defined above, additionally comprising step of selecting the magnetic field intensity B of each pulse applied by said step of applying pulsed electromagnetic therapy to said region to be higher than about 0 and lower than about max magnetic field used in MRI devices (i.e., 3 Tesla).

It is another object of the present invention to provide the methods as defined above, additionally comprising step of selecting the frequency F applied by the pulses applied by said step of applying pulsed electromagnetic therapy to said region to be higher than about 1 and lower than about 1M Hz.

It is another object of the present invention to provide the methods as defined above, additionally comprising step of selecting the energy E applied by said step of applying pulsed electromagnetic therapy to said region to be higher than about 1 and lower than about 150 watts per pulse.

It is another object of the present invention to provide the methods as defined above, wherein step of applying heat is applied for about 0.01 to 60 minutes.

It is another object of the present invention to provide the methods as defined above, wherein the heat and the pulsed electromagnetic therapy are applied simultaneously, sequentially or separately.

It is another object of the present invention to provide the methods as defined above, wherein said method is repeated 1 to 100 times in each treatment.

It is another object of the present invention to provide the methods as defined above, wherein said treatment is repeated more than once.

It is another object of the present invention to provide the methods as defined above, wherein said step of applying heat is performed by devices selected from a group consisting of: ultrasonic diathermy, an optical device, electromagnetic induction, sound waves emitting instrument, direct heat applying instrument, or from any other means of heating subcutaneous tissue to temperature T.

It is another object of the present invention to provide the methods as defined above, especially adapted to increase skin rejuvenation in the immediate (short) range It is another object of the present invention to provide the methods as defined above, especially adapted to increase skin rejuvenation in the intermediate range.

It is another object of the present invention to provide the methods as defined above, especially adapted to increase skin rejuvenation in the long range.

It is another object of the present invention to provide the methods as defined above, wherein said method is especially adapted to operate according to IEC selected from a group consisting of IEC 60601-2-35, IEC 60601-2-33, IEC 60601-2-29, IEC 60601-2-9, IEC 60601-2-5, IEC 60601-2-3, IEC 60601-1-8, IEC 60601-1-6, IEC 60601-1-4, IEC 60601-1-3, IEC 60601-1-2, IEC 60601-1-1 or any combination thereof.

It is another object of the present invention to provide an integrated system (20) adapted to increase skin rejuvenation of a region of a patient's skin, said system comprising at least two electrodes (41) adapted to be placed on said region of a patient's skin; each of said electrodes is at least partially coiled via a coil 42; wherein each of said electrodes is adapted for both (i) providing electromagnetic pulses to said region of a patient's skin; and, (ii) applying heat up to temperature T to said region of a patient's skin; further wherein all of said electrodes are adapted to simultaneously provide said electromagnetic pulses to said region of a patient's skin and apply heat to said region of a patient's skin.

It is another object of the present invention to provide the integrated system as defined above, wherein said heat applied to said region of a patient's skin is obtained by emitting RF radiation or via producing electrical current absorbed by subcutaneous tissue.

It is another object of the present invention to provide the integrated system as defined above, wherein application of said system increases said skin rejuvenation such that said skin rejuvenation increase (SRI) is greater than the sum of said SRI provided by electromagnetic pulses increase and said SRI provided by said deep tissue diathermy device increase.

It is another object of the present invention to provide the integrated system as defined above, wherein said electromagnetic pulse is a triangular shaped at frequency of 25 Hz and intensity of 20 Gauss.

It is another object of the present invention to provide the integrated system as defined above, wherein said electromagnetic pulse is square shaped at a frequency of 16 Hz, duration of about 5 milliseconds and intensity of 12 Gauss.

It is another object of the present invention to provide the integrated system as defined above, wherein said system reduces side effects and/or harmful effects of said electromagnetic pulses and/or said deep tissue diathermy such that said reduction of said side effects and/or said harmful effects is greater than the sum of said reduction of said electromagnetic pulses and/or said reduction of said deep tissue diathermy.

It is another object of the present invention to provide the integrated system as defined above, wherein said system additionally comprising a control system (6) adapted to regulate said electromagnetic pulses and/or said electromagnetic pulses.

It is another object of the present invention to provide the integrated system as defined above, wherein said system is adapted to provide a dynamic magnetic field such that said electromagnetic pulses vary with time.

It is another object of the present invention to provide the integrated system as defined above, wherein the shape of said electromagnetic pulse is selected in a non-limiting manner from a group consisting of square wave, a sine wave, a triangular wave, sawtooth wave, ramp waves, spiked wave or any other mathematical combination.

It is another object of the present invention to provide the integrated system as defined above, wherein the magnetic field intensity B of each pulse applied by said pulsed electromagnetic frequency generator (2) ranges between about 0 and about 3 Tesla.

It is another object of the present invention to provide the integrated system as defined above, wherein the duration of each pulse applied by said system ranges between about 3 and about 1000 milliseconds.

It is another object of the present invention to provide the integrated system as defined above, wherein the frequency F applied by the pulses of said system ranges between about 1 Hz and about 1M Hz.

It is another object of the present invention to provide the integrated system as defined above, wherein the energy E applied by the pulses of said system ranges between about 1 and about 150 watts per pulse.

It is another object of the present invention to provide the integrated system as defined above, wherein said temperature T is higher than about 30 and lower than about 80 degrees.

It is another object of the present invention to provide the integrated system as defined above, wherein said power supply and control system (6) monitors physical tissue parameters and changes applied heat and electromagnetic pulses accordingly.

It is another object of the present invention to provide the integrated system as defined above, wherein said power supply and control system (6) additionally comprising:
   a. processing means, adapted to store in a communicable database predetermined parameters defining (i) safe treatment parameters and (ii) unsafe treatment parameters; said parameters are selected from a group consisting of time t of said treatment, temperature T of said tissue, ratio t/T, Frequency F, power P, energy E applied by the pulses of said pulsed electromagnetic frequency generator, depth D of said treated tissue, magnetic field intensity B, tissue impedance, specific absorption rate (SAR), treatment depth, superficial muscle contractions or a combination thereof;
   b. sensing means; adapted to sense electromagnetic radiation and heat radiation parameters selected from a group consisting of time t of time t of said treatment, temperature T of said tissue, ratio t/T, Frequency F, power P, Intensity I of said ultrasound irradiation, energy E applied by the pulses of said pulsed electromagnetic frequency generator, depth D of said treated tissue, magnetic field intensity B, tissue impedance, specific absorption rate (SAR), treatment depth, superficial muscle contractions or a combination thereof;
   c. regulating means, adapted to allow said electromagnetic radiation and heat radiation if said parameters are within said safe treatment parameters and to stop the electromagnetic radiation if the radiation parameters are in said unsafe treatment parameters.

It is another object of the present invention to provide the integrated system as defined above, wherein said power supply and control system (6) includes a mechanism for skin cooling.

It is another object of the present invention to provide the integrated system as defined above, especially adapted to increase skin rejuvenation in the immediate (short) range.

It is another object of the present invention to provide the integrated system as defined above, especially adapted to increase skin rejuvenation in the intermediate range.

It is another object of the present invention to provide the integrated system as defined above, especially adapted to increase skin rejuvenation in the long range.

It is another object of the present invention to provide the integrated system as defined above, wherein said system is especially adapted to operate according to IEC selected from a group consisting of IEC 60601-2-35, IEC 60601-2-33, IEC 60601-2-29, IEC 60601-2-9, IEC 60601-2-5, IEC 60601-2-3, IEC 60601-1-8, IEC 60601-1-6, IEC 60601-1-4, IEC 60601-1-3, IEC 60601-1-2, IEC 60601-1-1 or any combination thereof.

It is another object of the present invention to provide a method of increasing skin rejuvenation of a region of a patient's skin. The method comprises steps selected inter alia from:
   a. obtaining an integrated system (20) adapted to increase skin rejuvenation; said integrated system (20) comprises: at least two electrodes (41) adapted to be placed on said region of a patient's skin; each of said electrodes is a least partially coiled via a coil 42;
   b. applying heat to a subcutaneous tissue within said region up to temperature T whilst simultaneously applying pulses of electromagnetic field to said region;
wherein said increasing of said skin rejuvenation is greater than the sum of said applying heat to a subcutaneous tissue within said region and said applying pulses electromagnetic therapy to said region It is another object of the present invention to provide the method as defined above, wherein said step of applying heat to a subcutaneous tissue within said region up to temperature T additionally comprising step of applying electrical current absorbed by subcutaneous tissue.

It is another object of the present invention to provide the method as defined above, wherein said system reduces side effects and/or harmful effects of said electromagnetic pulses and/or said deep tissue diathermy such that said reduction of said side effects and/or said harmful effects is greater than the sum of said reduction of said electromagnetic pulses and/or said reduction of said deep tissue diathermy.

It is another object of the present invention to provide the method as defined above, additionally comprising step of monitoring and/or controlling said steps of applying heat to a subcutaneous tissue within said region and/or said step of applying pulsed electromagnetic therapy to said region.

It is another object of the present invention to provide the method as defined above, additionally comprising step of applying a dynamic magnetic field onto said region.

It is another object of the present invention to provide the method as defined above, additionally comprising step of applying a triangular shaped electromagnetic pulse at frequency of 25 Hz and intensity of 20 Gauss.

It is another object of the present invention to provide the method as defined above, additionally comprising step of applying a square shaped electromagnetic pulse at a frequency of 16 Hz, duration of about 5 milliseconds and intensity of 12 Gauss.

It is another object of the present invention to provide the method as defined above, additionally comprising steps of
   a. storing in a communicable database predetermined parameters defining (i) safe treatment parameters and (ii) unsafe treatment parameters; said parameters are selected from a group consisting of time t of said treatment, temperature T of said tissue, ratio t/T, Frequency F, power P, energy E applied by the pulses of said pulsed electromagnetic frequency generator, depth D of said treated tissue, magnetic field intensity B, tissue impedance, specific absorption rate (SAR), treatment depth, superficial muscle contractions or a combination thereof;
   b. sensing electromagnetic radiation and heat radiation parameters selected from a group consisting of time t of said treatment, temperature T of said tissue, ratio t/T, Frequency F, power P, Intensity I of said ultrasound irradiation, energy E applied by the pulses of said pulsed electromagnetic frequency generator, depth D of said treated tissue, magnetic field intensity B, tissue impedance, specific absorption rate (SAR), treatment depth, superficial muscle contractions or a combination thereof;

c. allowing said electromagnetic radiation and said heat radiation if parameters within said safe treatment parameters and to stop the electromagnetic radiation if the radiation parameters are in said unsafe treatment parameters.

It is another object of the present invention to provide the method as defined above, additionally comprising step of selecting the shape of said electromagnetic pulse is selected in a non-limiting manner from a group consisting of square wave, a sine wave, a triangular wave, sawtooth wave, ramp waves, spiked wave or any other mathematical combination.

It is another object of the present invention to provide the method as defined above, additionally comprising step of selecting said temperature T from a region of about 30 to about 80 degrees.

It is another object of the present invention to provide the method as defined above, additionally comprising step of selecting the duration of each pulse applied by said pulsed electromagnetic frequency generator (2) to be higher than about 3 and lower than about 1000 milliseconds.

It is another object of the present invention to provide the method as defined above, additionally comprising step of selecting the magnetic field intensity B of each pulse applied by said step of applying pulsed electromagnetic therapy to said region to be higher than about 0 and lower than about 3 Tesla.

It is another object of the present invention to provide the method as defined above, additionally comprising step of selecting the frequency F applied by the pulses applied by said step of applying pulsed electromagnetic therapy to said region to be higher than about 1 and lower than about 1M Hz.

It is another object of the present invention to provide the method as defined above, additionally comprising step of selecting the energy E applied by said step of applying pulsed electromagnetic therapy to said region to be higher than about 1 and lower than about 150 watts per pulse.

It is another object of the present invention to provide the method as defined above, wherein step of applying heat is applied for about 0.01 to 60 minutes.

It is another object of the present invention to provide the method as defined above, wherein the heat and the pulsed electromagnetic therapy are applied simultaneously, sequentially or separately.

It is another object of the present invention to provide the method as defined above, wherein said method is repeated 1 to 100 times in each treatment.

It is another object of the present invention to provide the method as defined above, wherein said treatment is repeated more than once.

It is another object of the present invention to provide the method as defined above, wherein said step of applying heat is performed by devices selected from a group consisting of: ultrasonic diathermy, an optical device, electromagnetic induction, sound waves emitting instrument, direct heat applying instrument, or from any other means of heating subcutaneous tissue to temperature T.

It is another object of the present invention to provide the method as defined above, especially adapted to increase skin rejuvenation in the immediate (short) range It is another object of the present invention to provide the method as defined above, especially adapted to increase skin rejuvenation in the intermediate range.

It is still another object of the present invention to provide the method as defined above, especially adapted to increase skin rejuvenation in the long range.

It is lastly an object of the present invention to provide the method as defined above, wherein said method is especially adapted to operate according to IEC selected from a group consisting of IEC 60601-2-35, IEC 60601-2-33, IEC 60601-2-29, IEC 60601-2-9, IEC 60601-2-5, IEC 60601-2-3, IEC 60601-1-8, IEC 60601-1-6, IEC 60601-1-4, IEC 60601-1-3, IEC 60601-1-2, IEC 60601-1-1 or any combination thereof.

BRIEF DESCRIPTION OF THE DRAWINGS

In order to understand the invention and to see how it may be implemented in practice, a few preferred embodiments will now be described, by way of non-limiting example only, with reference to the accompanying drawings, in which:

FIGS. 13A-13F are pictures of one patient out of the study group treated with the device of the present invention.

FIGS. 16A-16F are pictures of one patient out of the third control group treated with the device of the present invention on the right side. The left side was treated with PEMF followed by RF.

DETAILED DESCRIPTION

Figure 1A:
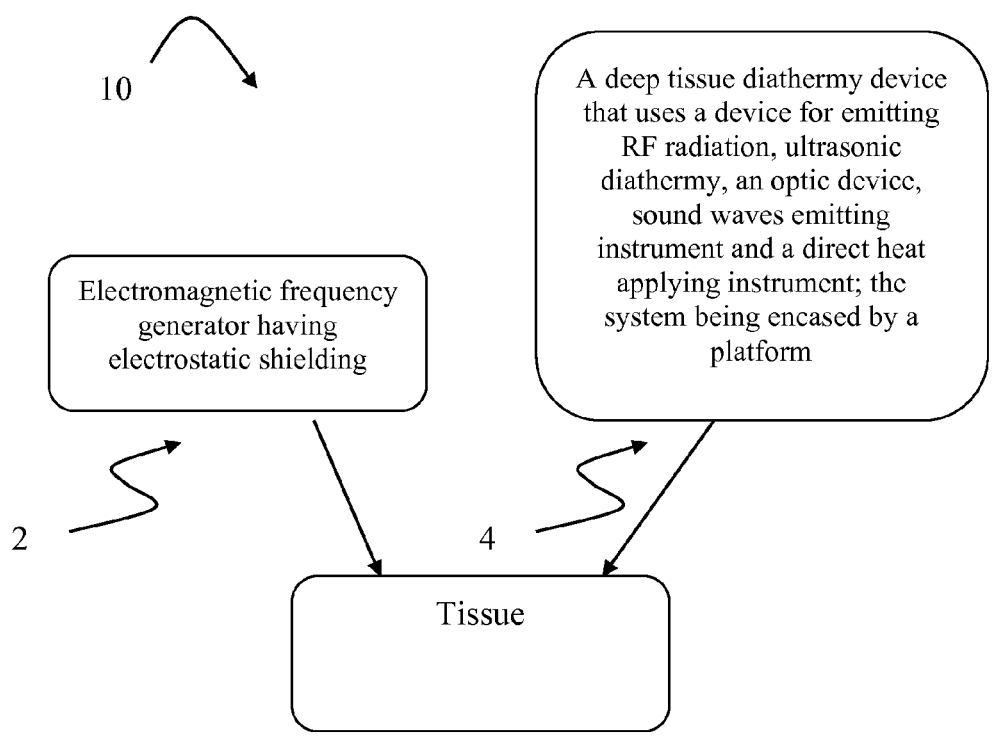
FIGS. 1A-1D schematically present a skin viability improving system (10), comprising a pulsed electromagnetic frequency generator (2) and a deep tissue diathermy device (4).

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide means and method for increasing the viability of the skin. Yet more the present invention provides means and system for skin tightening and rejuvenation.

It is one object of the present invention to disclose a device used to improve skin viability, by a synergistic approach of deep tissue diathermy combined with application of PEMF, wherein at least two devices of deep tissue diathermy are incorporated, one of them based on PEMF therapy. The latter improves the healing process initiated by the at least one other device of deep tissue diathermy.

The term "Pulsed Electromagnetic Fields (PEMF)" refers hereinafter in a non-limiting manner to electromagnetic radiation of different frequencies—ranging from static magnetic fields, through extremely low frequencies (ELF) to radiofrequencies (RF)—administered in pulses.

The term "Radio Frequency (RF)" refers hereinafter in a non-limiting manner to part of the electromagnetic spectrum with frequency range of about 3 Hz to 300 GHz.

The term "Extremely Low Frequencies (ELF)" refers hereinafter in a non-limiting manner to part of the RF electromagnetic spectrum with frequency range of about 3 Hz to 30 GHz.

The term "collagen" refers hereinafter in a non-limiting manner to a long, fibrous structural protein which is a major component of the extracellular matrix that supports most tissues and gives cells structure. It is responsible for skin strength and elasticity, and its degradation leads to wrinkles that accompany aging.

The term "epidermis" refers hereinafter in a non-limiting manner to the outermost layer of the skin.

The term "dermis" refers hereinafter in a non-limiting manner to a layer of skin beneath the epidermis that consists of connective tissue, and cushions the body from stress and strain.

The term "deep tissue diathermy" refers hereinafter in a non-limiting manner to a device which heats tissues beneath the epidermis.

The term "electric diathermy" refers hereinafter in a non-limiting manner to a device which uses high frequency alternating electric or magnetic fields, sometimes with no electrode or device contact to the skin, to induce gentle deep tissue heating by induction. For collagen fiber stimulation, typical electrical parameters may include, in a non limiting manner, frequency of about 1 MHz, energy of about 80 joule per 1 square tissue volume, applied for about 6 seconds.

The term "ultrasonic diathermy" refers hereinafter in a non-limiting manner to heating of tissues by ultrasound.

The term "about" refers hereinafter to a range of 25% below or above the referred value.

The term "physical tissue parameters" refers hereinafter to parameters such as tissue temperature, electric current, tissue impedance, specific absorption rate (SAR), treatment depth and superficial muscle contractions.

The term "angiogenesis" refers hereinafter to the sprouting of new blood vessels.

The term "square wave" refers hereinafter to a non-sinusoidal waveform named for its triangular shape.

The term "triangle wave" refers hereinafter to a non-sinusoidal waveform named for its triangular shape.

The term "International Electrotechnical Commission Standards (IEC) 60601-1" refers hereinafter to a medical electrical equipment standard. More specifically it refers to general requirements for basic safety and essential performance.

The term "IEC 60601-1-1" refers hereinafter to medical electrical equipment standard. More specifically it refers to general requirements for safety—Collateral standard: Safety requirements for medical electrical systems. The IEC 60601-1 set of standards are divided into three distinct areas. The first area is the basic standard IEC 60601-1. This is the general requirement for all electrical medical based products. The second area is the collateral standards, which cover across the board issues such as combining into a system with other devices, EMC, radiation protection, and programmable electronic medical systems (software, firmware, etc.). The standard numbers are IEC 60601-1-1, -1-2, -1-3, and -1-4 respectively. The third area is the particular standards that deal with a specific type of medical device. The particular standards are identified as IEC 60601-2-XX where XX identifies the particular standard number for the particular type of medical equipment. An example would be IEC 60601-2-3 which is the particular standard for short-wave therapy equipment.

The term "IEC 60601-1-2" refers hereinafter to medical electrical equipment standard. More specifically it refers to general requirements for basic safety and essential performance—Collateral standard: Electromagnetic compatibility—Requirements and tests.

The term "IEC 60601-1-3" refers hereinafter to medical electrical equipment standard. More specifically it refers to general requirements for basic safety and essential performance—Collateral Standard Radiation protection in diagnostic X-ray equipment.

The term "IEC 60601-1-4" refers hereinafter to medical electrical equipment standard. More specifically it refers to general requirements for safety—Collateral Standard: Programmable electrical medical systems.

The term "IEC 60601-1-6" refers hereinafter to medical electrical equipment standard. More specifically it refers to general requirements for basic safety and essential performance—Collateral standard: Usability.

The term "IEC 60601-1-8" refers hereinafter to medical electrical equipment standard. More specifically it refers to general requirements for basic safety and essential performance—Collateral Standard General requirements, tests and guidance for alarm systems in medical electrical equipment and medical electrical systems.

The term "IEC 60601-2-3" refers hereinafter to medical electrical equipment standard. More specifically it refers to particular requirements for the safety of short-wave therapy equipment.

The term "IEC 60601-2-5" refers hereinafter to medical electrical equipment standard. More specifically it refers to particular requirements for the safety of ultrasonic physiotherapy equipment.

The term "IEC 60601-2-9" refers hereinafter to medical electrical equipment. More specifically it refers to particular requirements for the safety of patient contact dosemeters used in radiotherapy with electrically connected radiation detectors.

The term "IEC 60601-2-29" refers hereinafter to medical electrical equipment standard. More specifically it refers to particular requirements for the basic safety and essential performance of radiotherapy simulators.

The term "IEC 60601-2-33" refers hereinafter to medical electrical equipment standard. More specifically it refers to particular requirements for the safety of magnetic resonance equipment for medical diagnosis.

The term "IEC 60601-2-35" refers hereinafter to medical electrical equipment standard. More specifically it refers to particular requirements for the safety of blankets, pads and mattresses intended for heating in medical use.

The present invention relates to a physical therapeutic methods and systems. In said systems a dynamic magnetic pulse and electromagnetic heating systems are incorporated together to accomplish a physical therapy, epically skin tightening and rejuvenation.

The present invention provides a system adapted to increase skin rejuvenation of a region of a patient's skin. The system comprising in a non-limiting manner the following:

a. a pulsed electromagnetic field (PEMF) frequency generator (2) for constantly providing electromagnetic pulses to said region of a patient's skin; and, b. a deep tissue diathermy device (4) applying heat to said region of a patient's skin up to temperature T;

The system (10) is adapted for simultaneously apply heat and PEMF to said region of a patient's skin. Furthermore, the system increases the skin rejuvenation such that the increase is greater than the sum of the electromagnetic pulses increase and the deep tissue diathermy.

Furthermore the system reduces side effects and/or harmful effects of the electromagnetic pulses and/or said deep tissue diathermy such that said reduction of said side effects and/or said harmful effects is greater than the sum of said reduction of said electromagnetic pulses and/or said reduction of said deep tissue diathermy.

It is another object of the present invention to provide an integrated system (20) adapted to increase skin rejuvenation of a region of a patient's skin. The system comprising at least two electrodes adapted to be placed on said region of a patient's skin; each of said electrodes is at least partially coiled via a coil. It is emphasized that each of said electrodes is adapted for both (i) providing electromagnetic pulses to said region of a patient's skin; and, (ii) applying heat up to temperature T to said region of a patient's skin. Furthermore, it is emphasized that all of said electrodes are adapted to simultaneously provide electromagnetic pulses to said region of a patient's skin; and, apply heat up to temperature T to said region of a patient's skin.

The decrease in the side effects of the deep tissue diathermy by the healing effect of the pulsed electromagnetic frequency therapy.

Reference is now made to FIGS. 1a-1d, illustrating the system 10 for increasing skin rejuvenation. As described above, the system comprising a pulsed electromagnetic frequency generator (2) for providing electromagnetic pulses to the region of a patient's skin; and, a deep tissue diathermy device (4) adapted to apply heat to the region of a patient's skin up to temperature T.

It is emphasized that the system increases the skin rejuvenation such that the increase is greater than the sum of the electromagnetic pulses increase and the deep tissue diathermy.

By exposing the tissue (a region of a patient's skin) to the combination of regulated heat and a pulsed electromagnetic filed a synergic effect of improving skin rejuvenation is obtained.

The present invention relays on 2 effects, the thermal effect and the electromagnetic pulse effect:

The thermal effect includes heating the tissue such that when the tissue is heated to a sufficiently high temperature, tissue injury is produced. Furthermore, when heat is generated within the dermis, it usually causes contraction and thickening of collagen fibers. This results in an overall tightened and rejuvenated appearance of the skin.

Heat within the dermis creates a limited thermal injury. The body's natural response to this injury is to produce collagen at the site of the wound. This results in firmer, thicker, more youthful skin. Usually the skin is heated to temperatures bellow 60 degrees for short periods of time. The thermal effect i.e., can be produced by:

1. Optical means—by emitting light in different wavelengths absorbed by subcutaneous tissue such that said tissue is heated; or
2. Electrical means—by passing electrical current; or
3. Electromagnetic means—by transmitting or inducting (electromagnetic induction) electromagnetic filed on the skin; or
4. Sound waves—specifically in the ultrasound frequencies; or
5. Physical means—such as massage or applying warm substance adjacent to the skin; or any combination thereof.

The electromagnetic pulses (either dynamic or static) may start natural healing processes which usually occur in response to an injury (especially, angiogenesis, and generation of new collagen fibers via the release of tissue growth factors).

Said electromagnetic field generates movements of charged molecules (ions) within the inter cellular fluids. This movement generates heat which may enhance the thermal effect discussed earlier.

It is acknowledged that healing is the process by which the cells in the body regenerate and repair to reduce the size of a damaged area. Healing incorporates both the removal of necrotic tissue (demolition), and the replacement of this tissue.

The replacement can happen in two ways:
1. by regeneration: the necrotic cells are replaced by the same tissue as was originally there.
2. by repair: injured tissue is replaced with scar tissue.

The Pulsed Electromagnetic Fields (PEMF) applied by the system 10, as described above, has no thermal effects. Said no thermal effects rely on the tissue components and their reaction to the applied radiation characteristics. These effects might be due to the reaction of large charged molecules and various frequencies and frequency harmonies, charged small ions in the cell membranes affecting the cells function and reactions to hormones and chemical signals, charged small ions in the extracellular space and other purely understood mechanisms.

Furthermore, applying the radiation in pulses was also found to have non thermal effects. Yet more, only a specific combination of frequency, duty cycle and transmitted power achieve a specific tissue response.

It is now commonly accepted that electromagnetic fields (EMF) or PEMF are capable of initiating various healing processes and for treatment of pain and edema in superficial soft tissues two decades ago. [Rosch, P. J., Markov, M. S., eds. Bioelectromagnetic Medicine, Marcel Dekker, NY, 251-264].

The present invention utilizes PEMF (combined with heat applying source) for cosmetic purposes as described above. The important role of PEMF in the specific field intensities and frequencies increases epidermal collagen synthesis. This new formed collagen increases skin elasticity and rejuvenates its appearance. Furthermore, PEMF increases the degree of endothelial cell tubulization and proliferation, and augmented angiogenesis primarily by stimulating endothelial release of FGF-2, inducing paracrine and autocrine changes in the surrounding tissue. Angiogenesis, the sprouting of new blood vessels, increases blood flow to the tissue, which in turn increases oxygen and nutritional substances delivery to the tissue. This effect is most beneficial for an injured tissue, promoting rapid and improved healing. The growth factor released further enhances the healing process, both in quality and time of improvement.

The following discloser is a more detailed description of the two combined effects.

As disclosed earlier, the present invention discloses a system 10 which incorporates both regulated heating means and electromagnetic pulses.

As described above, the heat can be produced by:
1. Optical means—by emitting light in different wavelengths absorbed by subcutaneous tissue such that said tissue is heated.
2. Electrical means—by passing electrical current.
3. Electromagnetic means—by transmitting or inducting (electromagnetic induction) electromagnetic filed on the skin.
4. Sound waves—specifically in the ultrasound frequencies.
5. Physical means—such as massage or applying warm substance adjacent to the skin.

Figure 1B:
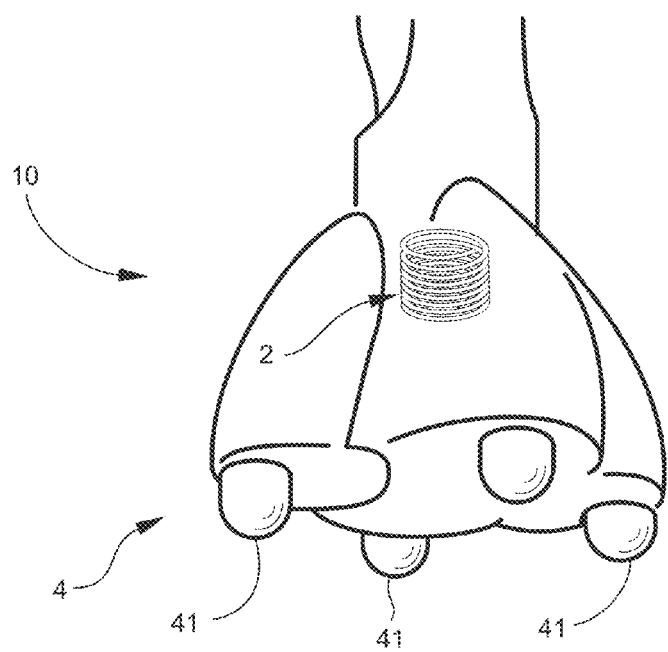
Figure 1C:
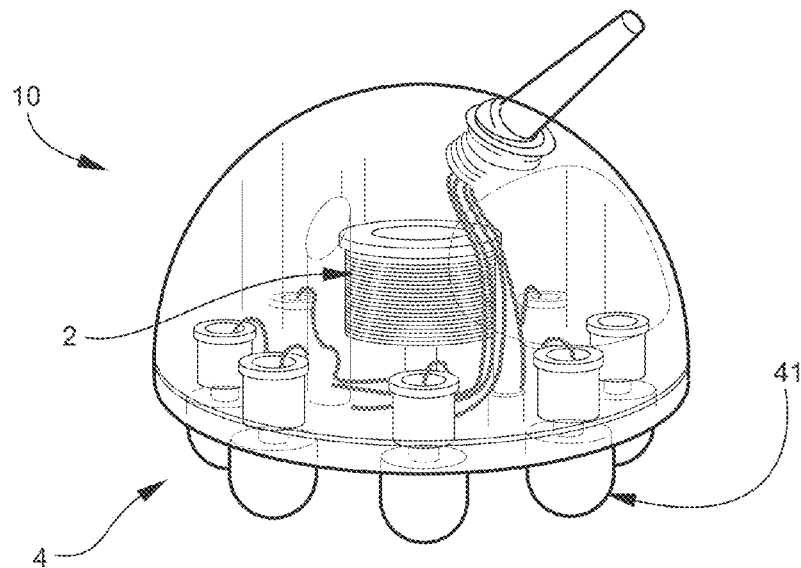
Figure 1D:
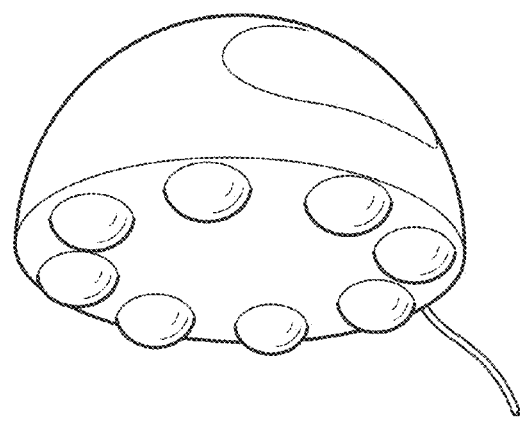

Reference is now made to FIGS. 1b-1d, illustrating the system 10 according to preferred embodiment of the present invention.

According to a preferred embodiment of the present invention, the deep tissue diathermy device (4) comprises:
  a. at least one electrical output device adapted to generate electrical current; and,
  b. at least two electrodes (41) electrically coupled to said electrical output device and placed on said skin region.

According to said embodiment all said electrodes are adapted to simultaneously apply said electrical current to said skin region.

FIG. 1b illustrates system 10 in which the deep tissue diathermy device (4) comprises 4 electrodes (denoted by numerical reference 41).

FIGS. 1c-1d illustrate the system 10 in which the deep tissue diathermy device (4) comprises 8 electrodes (denoted by numerical reference 41).

Figure 1E:
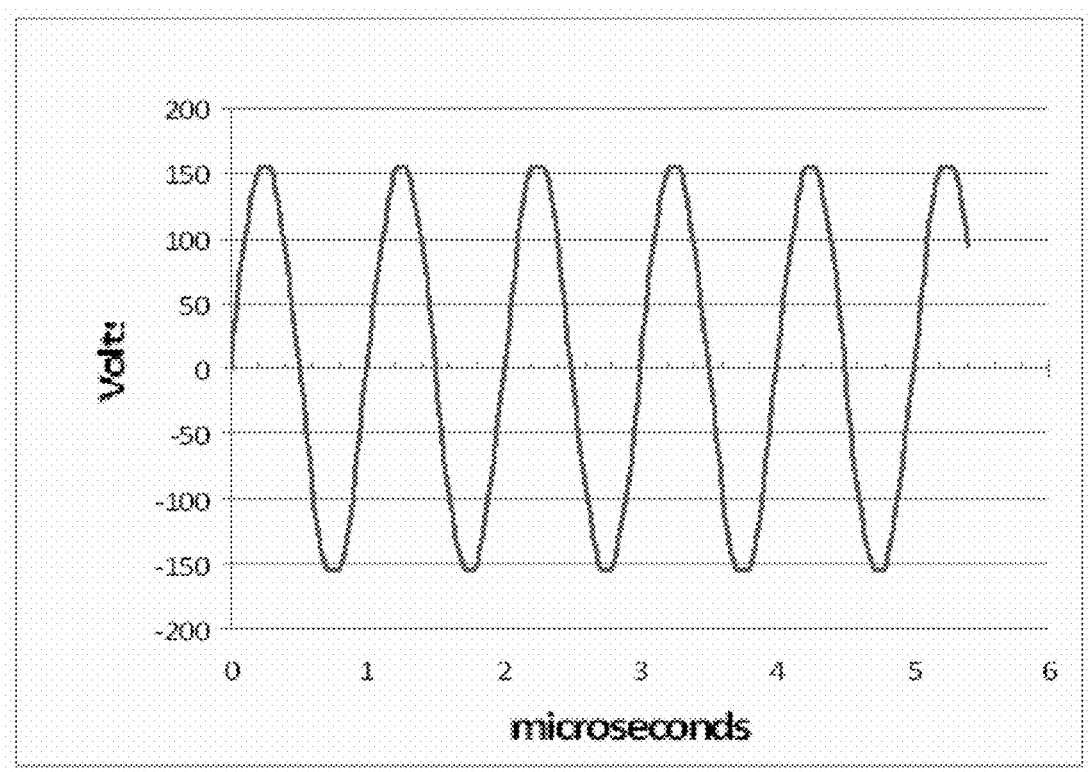
FIG. 1E is a diagram illustrating an example of electrical current applied by the deep tissue diathermy device (4). The current involves a maximal amplitude of 160 volts, and a frequency close to 1 Hz.

Reference is now made to FIG. 1e illustrating an example of electrical current applied by the deep tissue diathermy device (4). The current involves a maximal amplitude of 160 volts, and a frequency close to 1 Hz.

According to another embodiment of the present invention, the pulsed electromagnetic frequency generator is adapted to provide an electromagnetic field which varies with time (dynamic magnetic field).

According to another embodiment of the present invention, the pulsed electromagnetic frequency generator (2) which provides electromagnetic pulses to the patient's skin is positioned near the treated tissue and emits a dynamic magnetic field which varies with time. The dynamic magnetic field can vary according to any specific treatments. For examples, to stimulate angiogenesis, pulses at a frequency of 16 Hz, intensity of 12 Gauss and duration of about 5 milliseconds are generated. Alternatively, to stimulate collagen production a triangular wave pulses at a frequency of 25 Hz and intensity of 20 Gauss are generated.

The deep tissue diathermy device (4) is adapted to apply heat to said region of a patient's skin up to temperature T. According to one embodiment of the present invention the heat is applied by passing electrical current through the tissue. The electrical current can be performed in one of the following three manners:
  1. Through at least one electrode which is in direct physical contact with the skin;
  2. through at least one electrode which is not in physical contact with the skin, and the electrical current is transferred by induction.
  3. through at least one antenna which passes the electrical current to the skin via electromagnetic induction.

Figure 2:
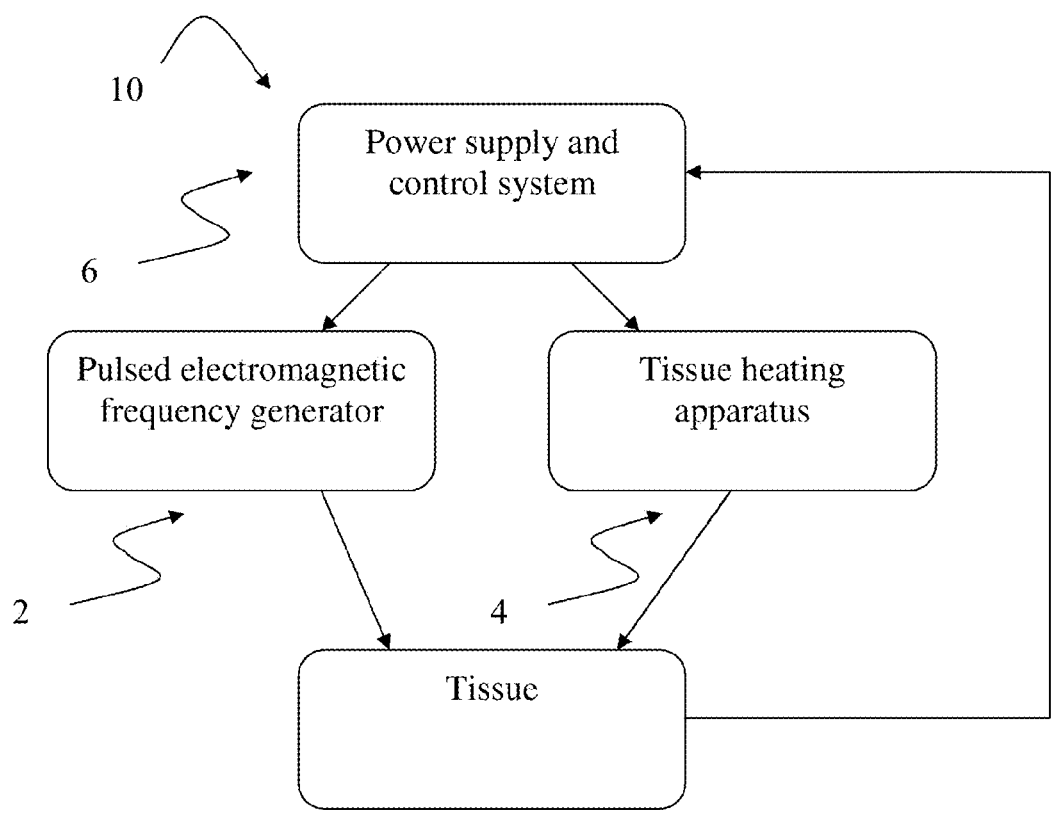
FIG. 2 schematically presents a skin viability improving system (10), comprising a pulsed electromagnetic frequency generator (2), a deep tissue diathermy device (4) and a power supply and control system (6).

Reference is now made to FIG. 2, which illustrates another embodiment of the present invention, According to that embodiment the system additionally comprising a control system (6) adapted to regulate said electromagnetic pulses and/or said electromagnetic pulses.

According to another embodiment of the present invention the treatment is provided only in safe treatment parameters.

Safe treatment parameters are defined by the parameters in table 1:

TABLE 1 safe treatment parameters

| parameter | Values |
| --- | --- |
| Time, t | 0-600 Minutes |
| Temperature, T | 25-80 Celsius |
| Duty cycle t/T | 0-100% |
| Frequency MHz | DC-10 Mhz |
| power P | 0-100 Watt |
| Energy E | 0-200 Jowls |
| magnetic field intensity B | 0-10 Tesla |
| Depth D of said treated tissue | 30 Millimeters |

Unsafe safe treatment parameters are defined by the parameters in table 2:

TABLE 2 unsafe treatment parameters

| parameter | Values |
| --- | --- |
| Time, t | >10 hours (none stop) |
| Temperature, T | >80 Celsius |
| Duty cycle t/T | N/A |
| Frequency MHz | >10 MHz |
| power P | >100 Watt |
| Energy E | >200 Jowls |
| magnetic field intensity B | >10 Tesla |
| Depth D of said treated tissue | >30 Millimeter |

According to another embodiment the, control system (6) additionally comprising:
(a) processing means, adapted to store in a communicable database predetermined parameters defining (i) safe treatment parameters and (ii) unsafe treatment parameters; said parameters are selected from a group consisting of time t of said treatment, temperature T of said tissue, duty cycle t/T, Frequency F, power P, Intensity I of said ultrasound diathermy, energy E applied by the pulses of said pulsed electromagnetic frequency generator, treatment depth D of said treated tissue, magnetic field intensity B, tissue impedance, specific absorption rate (SAR), superficial muscle contractions or a combination thereof;
(b) sensing means; adapted to sense electromagnetic radiation and heat radiation parameters selected from a group consisting of time t of time t of said treatment, temperature T of said tissue, duty cycle t/T, Frequency F, power P, Intensity I of said ultrasound diathermy, energy E applied by the pulses of said pulsed electromagnetic frequency generator, depth D of said treated tissue, magnetic field intensity B, tissue impedance, specific absorption rate (SAR), treatment depth, superficial muscle contractions or a combination thereof;
(c) regulating means, adapted to allow said pulsed electromagnetic radiation and heat radiation if said parameters are within said safe treatment parameters and to stop the pulsed electromagnetic radiation if the radiation parameters are in said unsafe treatment parameters.

According to another embodiment, the system as defined above, additionally comprising sensors for monitoring physical parameters selected form a group consisting of time t of said treatment, temperature T of said tissue, duty cycle t/T, Frequency F, power P, energy E applied by the pulses of said pulsed electromagnetic frequency generator, depth D of said treated tissue, magnetic field intensity B, tissue impedance, specific absorption rate (SAR), treatment depth, superficial muscle contractions or a combination thereof.

The sensors receives said parameters from the treated tissue and changes the parameters of the pulsed electromagnetic frequency generator (2) and the deep tissue diathermy device (4) to optimize the effect of each component and/or to augment the synergistic effect of both components, whilst avoiding harm to the tissue.

According to another embodiment of the present invention the shape of the electromagnetic pulse is selected in a non-limiting manner from a group consisting of square wave, a sine wave, a triangular wave, sawtooth wave, ramp waves, spiked wave or any other mathematical combination.

According to another embodiment, the system as defined above is adapted to provide electromagnetic pulse at a frequency of 16 Hz which increases from 0 Gauss to 12 Gauss. According to another embodiment, the system as defined above is adapted to provide electromagnetic square wave pulse at a frequency of 16 Hz which increases from 0 Gauss to 12 Gauss.

Figure 3:
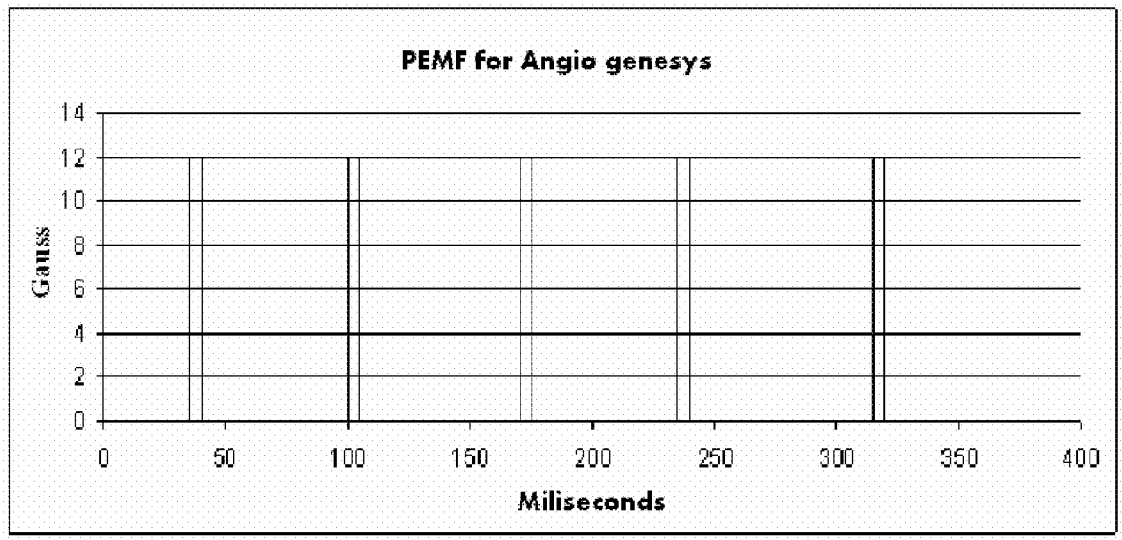
FIG. 3 schematically presents square waves at a rate of 16 Hz in duration of about 5 milliseconds in an intensity of 12 Gauss which stimulate angiogenesis.

According to another embodiment, the system as defined above is adapted to provide short square waves at a rate of 16 Hz in duration of about 5 milliseconds in an intensity of 12 Gauss. Such square wave pulses are especially provided to stimulate angiogenesis. Reference is now made to FIG. 3, which illustrates such square wave pulse.

Figure 4:
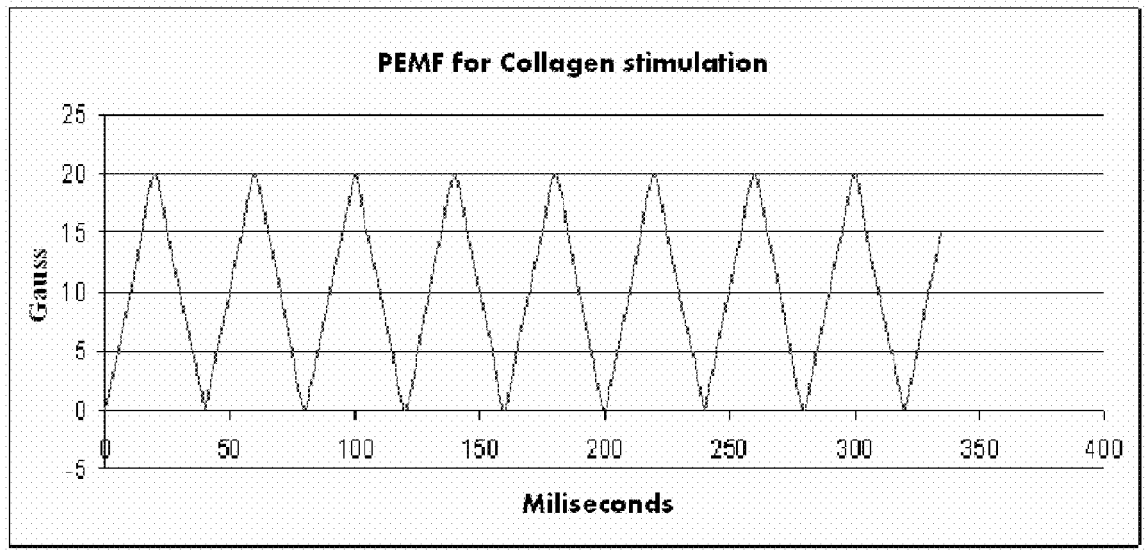
FIG. 4 schematically presents triangular wave pulses at a frequency of 25 Hz and intensity of 20 Gauss which stimulate collagen production.

According to another embodiment, the system as defined above is adapted to provide triangular wave pulses at a frequency of 25 Hz and intensity of 20 Gauss. Such pulses are especially provided to stimulate collagen production. Reference is now made to FIG. 4, which illustrates such triangular wave pulses.

According to another embodiment, the system as defined above is adapted to provide alternating current (AC) at a frequency of 1 MHz.

According to another embodiment, the system as defined above is adapted to provide intensity of about 80 J/cm$^2$ sec.

According to another embodiment of the present invention the magnetic field intensity B of each pulse applied by said pulsed electromagnetic frequency generator (2) ranges between about 0 and about the max magnetic field used in MRI devices (i.e., 3 Tesla).

According to another embodiment of the present invention, the duration of each pulse applied by said pulsed electromagnetic frequency generator (2) ranges between about 3 and about 1000 milliseconds.

According to another embodiment of the present invention, the frequency F applied by the pulses of said pulsed electromagnetic frequency generator (2) ranges between about 1 and about 1M Hz.

According to another embodiment of the present invention, the energy E applied by the pulses of said pulsed electromagnetic frequency generator (2) ranges between about 1 and about 150 watts per pulse.

According to another embodiment of the present invention, the deep tissue diathermy device (4) is selected in a non-limiting manner from a group consisting of electric diathermy or any device emitting RF radiation absorbed by subcutaneous tissue.

According to another embodiment of the present invention, the deep tissue diathermy device (4) is selected in a non-limiting manner from a group consisting of an ultrasonic diathermy, an optical device, electromagnetic induction, sound waves emitting instrument, direct heat applying instrument, or from any other means of heating subcutaneous tissue to temperature T.

According to another embodiment of the present invention, the optical device is adapted to emit light in wavelengths absorbed by subcutaneous tissue such that said subcutaneous tissue is heated.

According to another embodiment of the present invention, the sound waves emitting instrument is adapted to emit sound waves absorbed by the subcutaneous tissue such that said subcutaneous tissue is heated.

According to another embodiment of the present invention, the temperature T is higher than about 30 and lower than about 80 degrees.

According to another embodiment of the present invention, the power supply and control system (6) includes a mechanism for skin cooling.

According to another embodiment of the present invention, system (10) is encased in at least one platform.

According to another embodiment of the present invention, the pulsed electromagnetic frequency generator (2) and said deep tissue diathermy device (4) have more than one applicator to treat more than one body part simultaneously.

According to another embodiment of the present invention, the pulsed electromagnetic frequency generator (2) has electrostatic shielding.

Is should be emphasized that the system as defined in any of the embodiments produces synergic outcomes in the following three ranges:

The immediate (short) range, in the intermediate range and in the long range.

In the immediate (short) range—the contraction and thickening of collagen fibers occur, which in turn results in an overall tightened and rejuvenated appearance of the skin.

In the intermediate range (i.e., about two to three weeks)—new epidermal cells and new collagen fibers are produced.

In the long range (i.e., about a month)—the cellulite is scattered.

Figure 5:
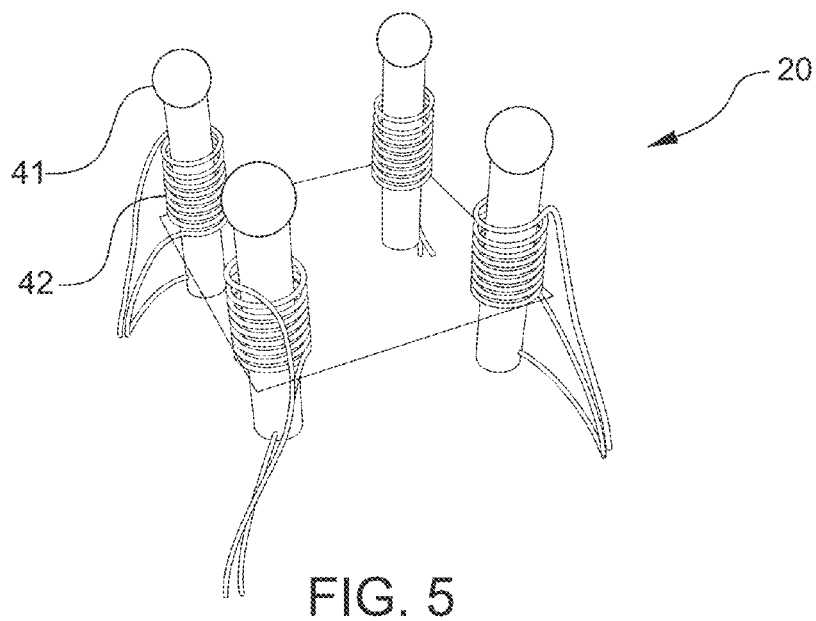
FIGS. 5-6 illustrate another embodiment of the skin viability improving system (20).
Figure 6:
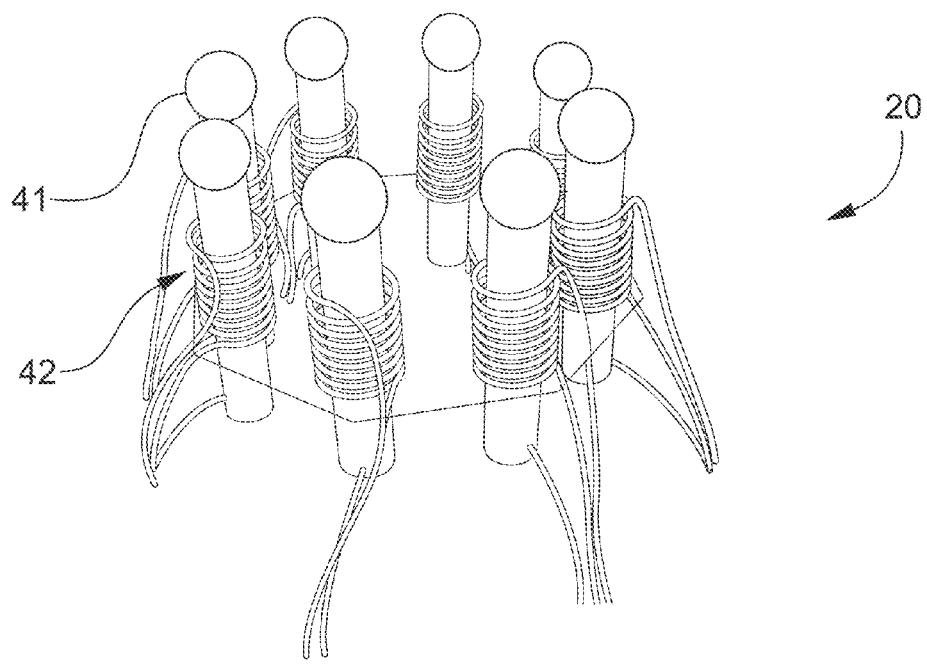

Reference is now made to FIGS. 5-6 illustrating another system (20) according to a preferred embodiment of the present invention. According to this embodiment, an integrated system (20) adapted to increase skin rejuvenation of a region of a patient's skin is provided.

The system 20 comprising at least two electrodes (41) adapted to be placed on said region of a patient's skin; each of said electrodes is a least partially coiled (or looped) via a coil (42).

It should be emphasized that each of said electrodes is adapted for both (i) providing electromagnetic pulses to said region of a patient's skin (via said coil); and, (ii) applying heat up to temperature T to said region of a patient's skin.

Furthermore, it should be emphasized that all said electrodes provide simultaneously electromagnetic pulses to said region of a patient's skin; and, apply heat up to temperature T to said region of a patient's skin.

The heat is provided to the skin by applying electrical current through said electrodes which is absorbed by subcutaneous tissue.

FIG. 5 illustrates such a system 20 comprising 4 electrodes (denotes as 41) and FIG. 6 illustrates such a system comprising 8 electrodes (denotes as 41).

It should be emphasized that the application of said system 20 increases said skin rejuvenation such that said skin rejuvenation increase (SRI) is greater than the sum of said SRI provided by electromagnetic pulses increase and said SRI provided by said deep tissue diathermy device increase.

According to another embodiment of the present invention the electromagnetic pulse in system 20 is a triangular shaped at frequency of 25 Hz and intensity of 20 Gauss.

According to another embodiment of the present invention the electromagnetic pulse in system 20 is square shaped at a frequency of 16 Hz, duration of about 5 milliseconds and intensity of 12 Gauss.

According to another embodiment of the present invention, the system 20 reduces side effects and/or harmful effects of said electromagnetic pulses and/or said deep tissue diathermy such that said reduction of said side effects and/or said harmful effects is greater than the sum of said reduction of said electromagnetic pulses and/or said reduction of said deep tissue diathermy.

According to another embodiment of the present invention, the system 20 additionally comprising a control system (6) adapted to regulate said electromagnetic pulses and/or said electromagnetic pulses.

According to another embodiment of the present invention, the system is adapted to provide a dynamic magnetic field such that said electromagnetic pulses vary with time.

According to another embodiment of the present invention, the shape of said electromagnetic pulse in system 20 is selected in a non-limiting manner from a group consisting of square wave, a sine wave, a triangular wave, sawtooth wave, ramp waves, spiked wave or any other mathematical combination.

According to another embodiment of the present invention, the magnetic field intensity B in system 20 of each pulse applied by said pulsed electromagnetic frequency generator (2) ranges between about 0 and about 3 Tesla.

According to another embodiment of the present invention, the duration of each pulse applied in system 20 ranges between about 3 and about 1000 milliseconds.

According to another embodiment of the present invention, the frequency F applied by the pulses of said system ranges between about 1 Hz and about 1M Hz.

According to another embodiment of the present invention, the energy E applied by said system ranges between about 1 and about 150 watts per pulse.

According to another embodiment of the present invention, the temperature T is higher than about 30 and lower than about 80 degrees.

According to another embodiment of the present invention, the power supply and control system (6) in system (20) monitors physical tissue parameters and changes applied heat and electromagnetic pulses accordingly.

According to another embodiment of the present invention, the power supply and control system (6) additionally comprising:
  a. processing means, adapted to store in a communicable database predetermined parameters defining (i) safe treatment parameters and (ii) unsafe treatment parameters; said parameters are selected from a group consisting of time t of said treatment, temperature T of said tissue, ratio t/T, Frequency F, power P, energy E applied by the pulses of said pulsed electromagnetic frequency generator, depth D of said treated tissue, magnetic field intensity B, tissue impedance, specific absorption rate (SAR), treatment depth, superficial muscle contractions or a combination thereof;
  b. sensing means; adapted to sense electromagnetic radiation and heat radiation parameters selected from a group consisting of time t of said treatment, temperature T of said tissue, ratio t/T, Frequency F, power P, Intensity I of said ultrasound irradiation, energy E applied by the pulses of said pulsed electromagnetic frequency generator, depth D of said treated tissue, magnetic field intensity B, tissue impedance, specific absorption rate (SAR), treatment depth, superficial muscle contractions or a combination thereof;
  c. regulating means, adapted to allow said electromagnetic radiation and heat radiation if said parameters are within said safe treatment parameters and to stop the electromagnetic radiation if the radiation parameters are in said unsafe treatment parameters.

According to another embodiment of the present invention, the power supply and control system (6) includes a mechanism for skin cooling.

According to another embodiment of the present invention, the system (20) is especially adapted to increase skin rejuvenation in the immediate (short) range.

According to another embodiment of the present invention, the system (20) is especially adapted to increase skin rejuvenation in the intermediate range.

According to another embodiment of the present invention, the system (20) is especially adapted to increase skin rejuvenation in the long range.

Figure 7:
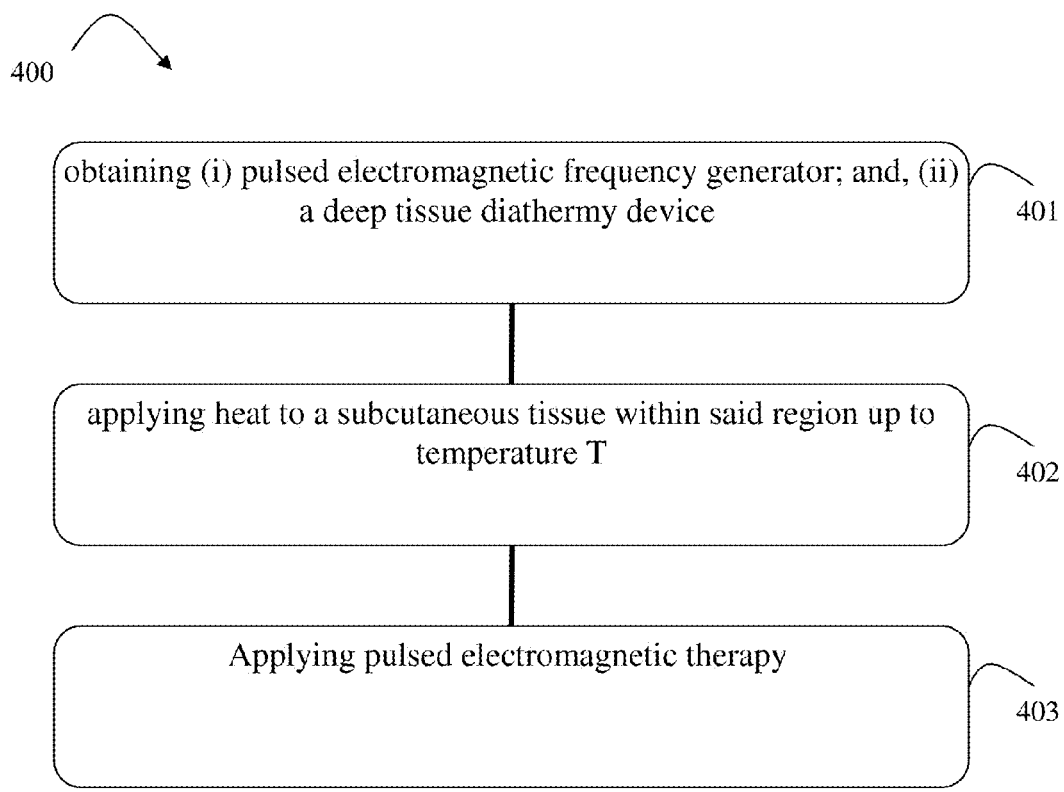
FIGS. 7-12 schematically present the methods of improving skin viability (400-420).

Reference is now made to FIG. 7, schematically illustrating one possible method (400) of increasing skin rejuvenation of a region of a patient's skin. The method comprising steps selected inter alia from obtaining (i) pulsed electromagnetic frequency generator; and, (ii) a deep tissue diathermy device (401); applying heat to a subcutaneous tissue within said region up to temperature T (402); said temperature T is optimized for production of new dermal ground substance and collagen contraction. While the collagen contraction tightens the skin and conceals wrinkles immediately, the dermal proliferation and new collagen production has a later effect.

The next step is applying additional pulsed electromagnetic field (403) which generates a healing mechanism of the heated skin, which includes growth factor and cytokines release and eventually angiogenesis.

Figure 8:
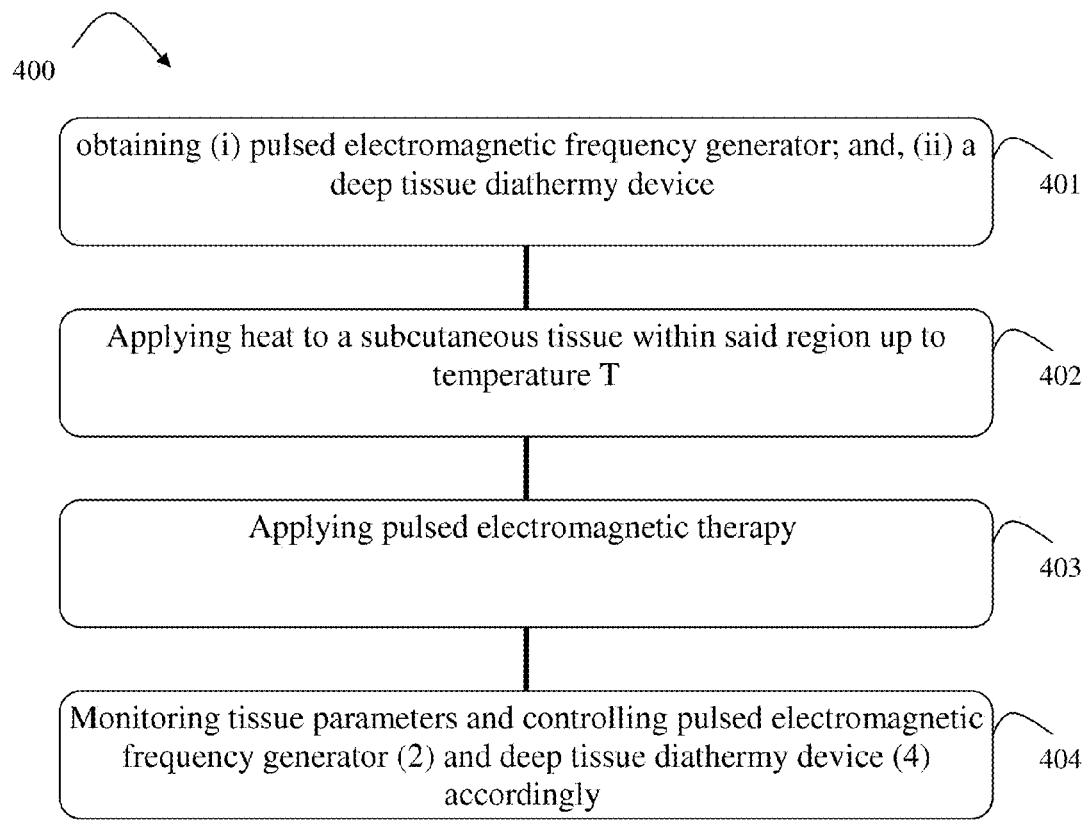
Figure 9:
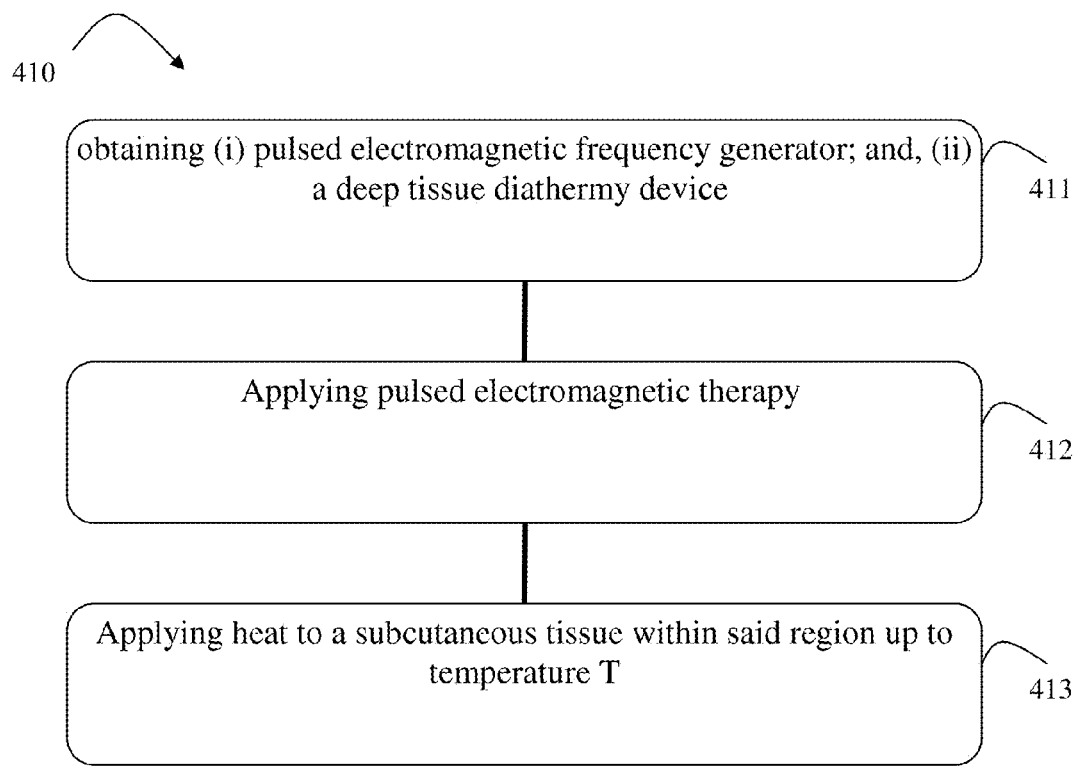

Reference is now made to FIG. 8, which illustrates another preferred method of the present invention. According to this embodiment, the method 400 additionally comprises the step of: monitoring and/or controlling said steps of applying heat to a subcutaneous tissue within said region and/or said step of applying pulsed electromagnetic therapy to said region (404). Reference is now made to FIG. 9, schematically illustrating one possible method (410) of increasing skin rejuvenation of a region of a patient's skin. The method comprising steps selected inter alia from obtaining (i) pulsed electromagnetic frequency generator; and, (ii) a deep tissue diathermy device (411). The next step is applying additional pulsed electromagnetic field (412) which generates a healing mechanism of the heated skin, which includes growth factor and cytokines release and eventually angiogenesis. The final step is applying heat to a subcutaneous tissue within said region up to temperature T (413); said temperature T is optimized for production of new dermal ground substance and collagen contraction. While the collagen contraction tightens the skin and conceals wrinkles immediately, the dermal proliferation and new collagen production has a later effect.

Figure 10:
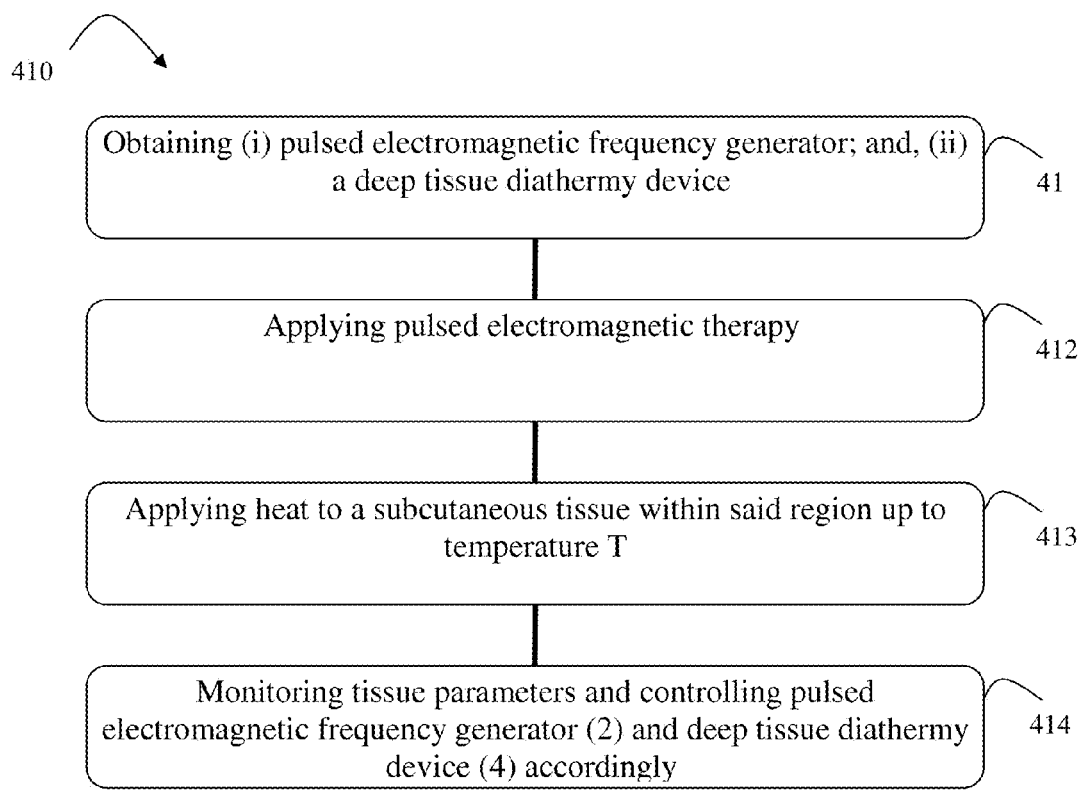
Figure 11:
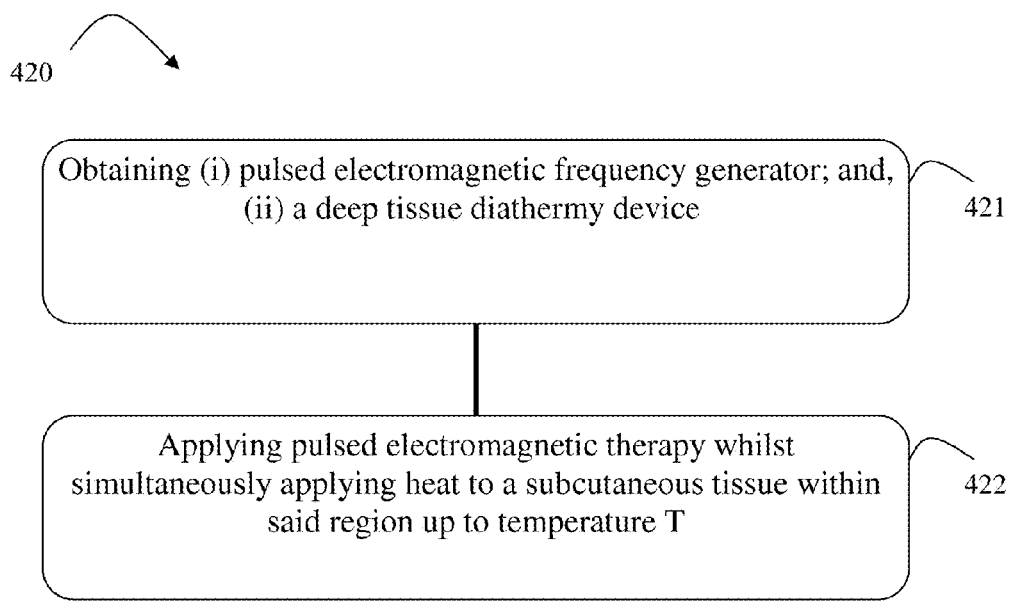

Reference is now made to FIG. 10, which illustrates another preferred method of the present invention. According to this embodiment, the method 410 additionally comprises the step of: monitoring and/or controlling said steps of applying heat to a subcutaneous tissue within said region and/or said step of applying pulsed electromagnetic therapy to said region (414). Reference is now made to FIG. 11, schematically illustrating one possible method (420) of increasing skin rejuvenation of a region of a patient's skin. The method comprising steps selected inter alia from obtaining (i) pulsed electromagnetic frequency generator; and, (ii) a deep tissue diathermy device (421). The next step is applying additional pulsed electromagnetic field (422) whilst simultaneously applying heat to a subcutaneous tissue within said region up to temperature T. The electromagnetic pulses generate a healing mechanism of the heated skin, which includes growth factor and cytokines release and eventually angiogenesis. The heat applied temperature T is optimized for production of new dermal ground substance and collagen contraction. While the collagen contraction tightens the skin and conceals wrinkles immediately, the dermal proliferation and new collagen production has a later effect.

Figure 12:
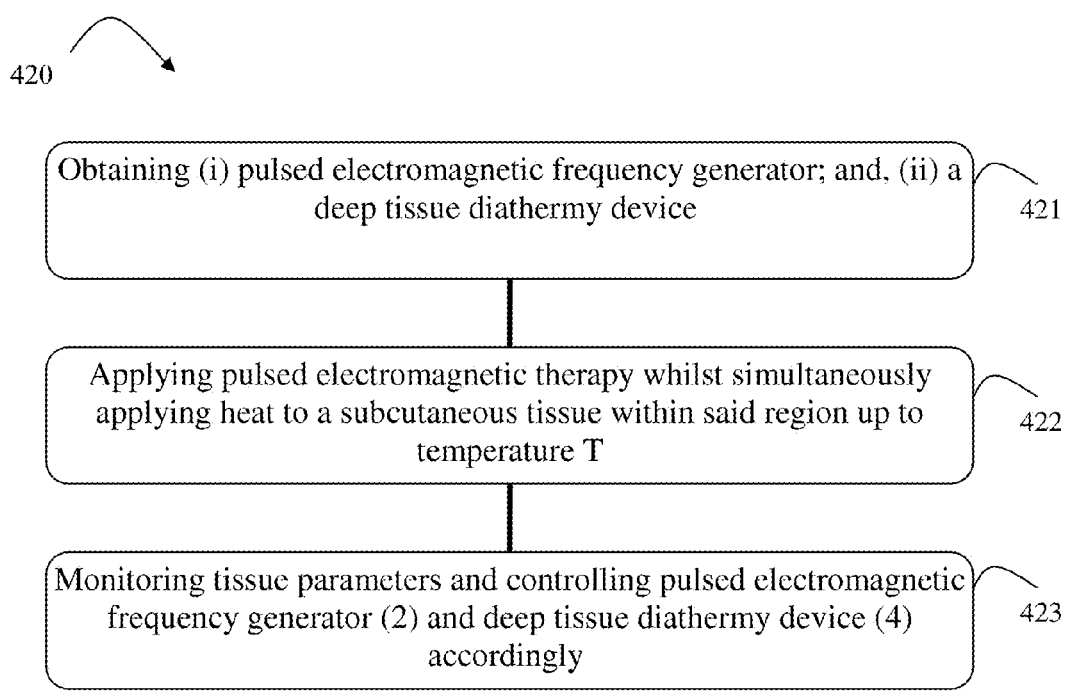
Figures 14A, 14C, 14E:
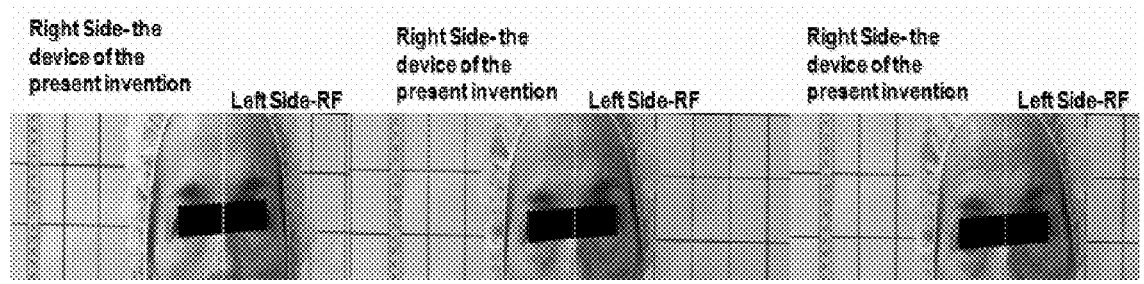
FIGS. 14A-14F are pictures of one patient out of the first control group treated with the device of the present invention on the right side and RF on the left side.
Figures 14B, 14D, 14F:
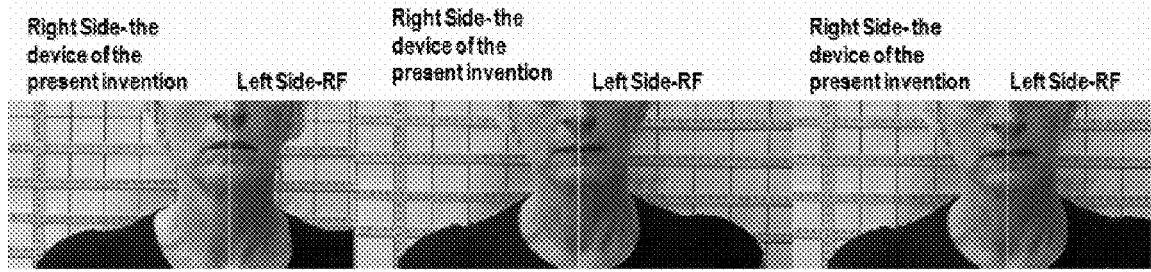
Figure 15E:
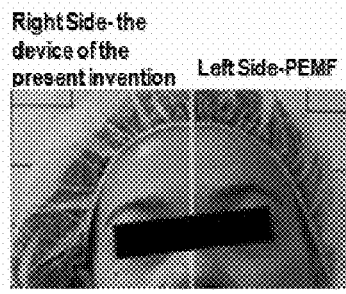
FIGS. 15A-15F are pictures of one patient out of the second control group treated with the device of the present invention on the right side and PEMF on the left side.
Figure 15C:
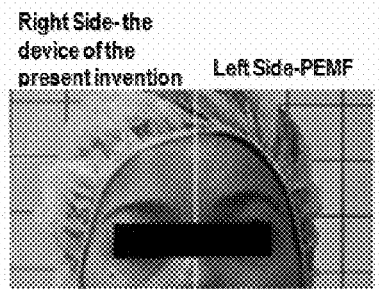
Figure 15A:
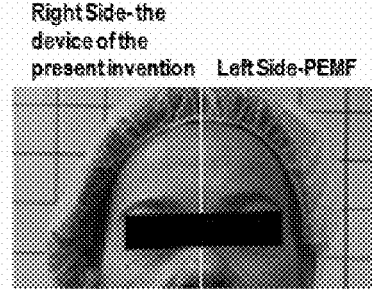
Figure 15F:
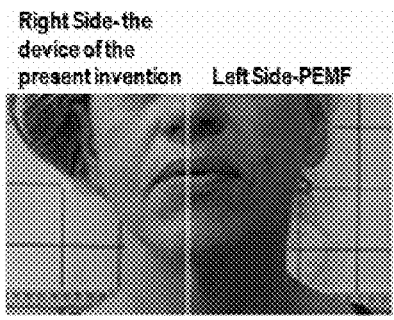
Figure 15D:
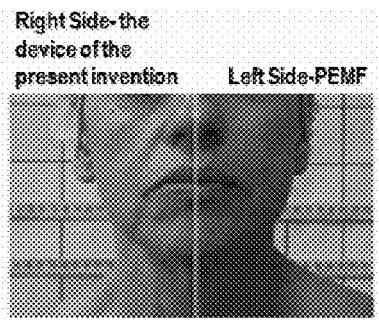
Figure 15B:
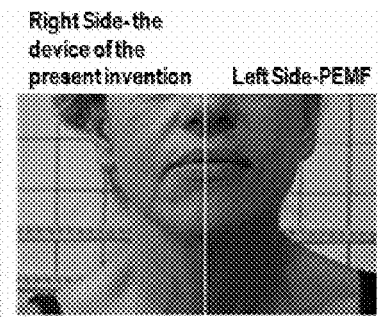

Reference is now made to FIG. 12, which illustrates another preferred method of the present invention. According to this embodiment, the method 420 additionally comprises the step of: monitoring and/or controlling said steps of applying heat to a subcutaneous tissue within said region and/or said step of applying pulsed electromagnetic therapy to said region (424).

According to another embodiment of the present invention, each of the methods as defined above additionally comprising step of selecting said temperature T from a region of about 30 to about 80 degrees.

According to another embodiment of the present invention, each of the methods as defined above additionally comprising step of applying a dynamic magnetic field onto said region.

According to another embodiment of the present invention, each of the methods as defined above additionally comprising steps of:
a. storing in a communicable database predetermined parameters defining (i) safe treatment parameters and (ii) unsafe treatment parameters; said parameters are selected from a group consisting of time t of said treatment, temperature T of said tissue, duty cycle t/T, Frequency F, power P, energy E applied by the pulses of said pulsed electromagnetic frequency generator, depth D of said treated tissue, magnetic field intensity B, tissue impedance, specific absorption rate (SAR), treatment depth, superficial muscle contractions or a combination thereof;
b. sensing electromagnetic radiation and heat radiation parameters selected from a group consisting of time t of time t of said treatment, temperature T of said tissue, duty cycle t/T, Frequency F, power P, Intensity I of said ultrasound diathermy, energy E applied by the pulses of said pulsed electromagnetic frequency generator, depth D of said treated tissue, magnetic field intensity B, tissue impedance, specific absorption rate (SAR), treatment depth, superficial muscle contractions or a combination thereof;
c. allowing said electromagnetic radiation and said heat radiation if parameters are within said safe treatment parameters and stopping the electromagnetic radiation if the radiation parameters are in said unsafe treatment parameters.

According to another embodiment of the present invention, the step of applying heat is performed by devices selected from a group consisting of: ultrasonic diathermy, an optical device, electromagnetic induction, sound waves emitting instrument, direct heat applying instrument, or from any other means of heating subcutaneous tissue to temperature T.

According to another embodiment of the present invention, each of the methods as defined above additionally comprising step of selecting the magnetic field intensity B of each pulse applied by said step of applying pulsed electromagnetic therapy to said region to be higher than about 0 and lower than about max magnetic field used in MRI devices (i.e., 3 Tesla).

According to another embodiment of the present invention, each of the methods as defined above additionally comprising step of selecting the frequency F applied by the pulses applied by said step of applying pulsed electromagnetic therapy to said region to be higher than about 1 Hz and lower than about 1 MHz.

According to another embodiment of the present invention, each of the methods as defined above additionally comprising step of selecting the energy E applied by said step of applying pulsed electromagnetic therapy to said region to be higher than about 1 and lower than about 150 watts per pulse.

According to another embodiment of the present invention, in each of the methods as defined above the step of applying heat lasts about 0.01 to 100 minutes.

According to another embodiment of the present invention, in each of the methods as defined above the pulsed electromagnetic field lasts about 0.01 to 100 minutes.

According to another embodiment of the present invention, in each of the methods as defined above the steps of applying heat and applying the pulsed electromagnetic therapy are simultaneous, sequential or separate.

According to another embodiment of the present invention, in each of the methods as defined above the method is repeated 1 to 100 times in each treatment.

According to another embodiment of the present invention, a typical protocol for the pulsed electromagnetic frequency generator (4) includes for example, and in a non limiting manner, a preset number of 1 microsecond period pulses with duty cycle of 50% and a pause of up to 250 microsecond (in which the preset number of pulses correlates with energy to be supplied to skin under the treatment.)

According to another embodiment of the present invention, a typical protocol for the pulsed electromagnetic frequency generator (4) includes for example, and in a non limiting manner 10 pulses, of 1 microsecond period with 50% duty cycle and preset pause of up to 512 microseconds (in which the pause correlates with energy to be supplied to skin under the treatment).

According to another embodiment of the present invention, a typical protocol for the pulsed electromagnetic frequency generator (4) includes for example, and in a non limiting manner, a repetition of the previous protocol, wherein the number of pulses administered is a multiplication of 10.

According to another embodiment of the present invention, in each of the methods as defined above the treatment is repeated more than once.

According to another embodiment of the present invention, each of the methods as defined above additionally comprising step of selecting the shape of said electromagnetic pulse is selected in a non-limiting manner from a group consisting of square wave, a sine wave, a triangular wave, sawtooth wave, ramp waves, spiked wave or any other mathematical combination.

It should also be appreciated that the above described description of methods and apparatus are to be interpreted as including apparatus for carrying out the methods, and methods of using the apparatus of any type as well known to a person or ordinary skill, and which need not be described in detail herein for enabling a person of ordinary skill to practice the invention.

For the main embodiments of the invention, the particular selection of type and model is not critical, though where specifically identified, this may be relevant. The present invention has been described using detailed descriptions of embodiments thereof that are provided by way of example and are not intended to limit the scope of the invention. No limitation, in general, or by way of words such as "may", "should", "preferably", "must", or other term denoting a degree of importance or motivation, should be considered as a limitation on the scope of the claims or their equivalents unless expressly present in such claim as a literal limitation on its scope. It should be understood that features and steps described with respect to one embodiment may be used with other embodiments and that not all embodiments of the invention have all of the features and/or steps shown in a particular figure or described with respect to one of the embodiments. That is, the disclosure should be considered complete from combinatorial point of view, with each embodiment of each element considered disclosed in conjunction with each other embodiment of each element (and indeed in various combinations of compatible implementations of variations in the same element). Variations of embodiments described will occur to persons of the art. Furthermore, the terms "comprise," "include," "have" and their conjugates, shall mean, when used in the claims, "including but not necessarily limited to." Each element present in the claims in the singular shall mean one or more element as claimed, and when an option is provided for one or more of a group, it shall be interpreted to mean that the claim requires only one member selected from the various options, and shall not require one of each option. The abstract shall not be interpreted as limiting on the scope of the application or claims.

It is noted that some of the above described embodiments may describe the best mode contemplated by the inventors and therefore may include structure, acts or details of structures and acts that may not be essential to the invention and which are described as examples.

Structure and acts described herein are replaceable by equivalents performing the same function, even if the structure or acts are different, as known in the art. Therefore, the scope of the invention is limited only by the elements and limitations as used in the claims.

EXAMPLES

Examples are given in order to prove the embodiments claimed in the present invention. The example, which is a clinical test, describes the manner and process of the present invention and set forth the best mode contemplated by the inventors for carrying out the invention, but are not to be construed as limiting the invention.

Example 1

A clinical test was performed to demonstrate the synergic effect of the combined PEMF and the deep tissue diathermy device.

The aim of the example is to evaluate the synergetic effect of the combined technology and compare it to each technology individually.

A multi polar magnetic pulsed synthesizer which simultaneously emits RF and magnetic pulses in varying phases that homogeneously cause supra normal temperatures over the treated area and penetrates the dermis and hypodermis was used.

Method

The test included 40 women at the age of 42-61 years.

They were divided to 4 groups; 1 study group and 3 control groups, each group included 10 clients. All participants were selected very punctiliously according to predefined criterions which included loosen skin in the forehead, eyes and neck area.

All groups were treated for skin tightening of the face (forehead & eyes) and neck. In all groups the right side of the face and neck was treated only by the use of combined technology and the left side of the face and neck was treated according the following:

Study group: the combined technology as well.
First control group: RF technology.
Second control group: PMF (Pulsed Magnetic Field) technology.
Third control group: PMF technology and 2 hours later RF technology.

Sessions were conduced once a week for a period of 8 weeks.

Each session lasted 40 minutes (20 minutes each side) except of the third control group which lasted 60 minutes (right side 20 minutes and left side 40 minutes because we used 2 different technologies).

Clinical results were collected in two paths; objective and subjective.

Objective Method

Objective method was conducted by taking photographs in order to assess the changes in the tightness of the skin induced by the treatments.

The pictures were taken before and after treatments by the same operator under the same conditions. The pictures were taken while the participant sat in front of a chart with vertical and horizontal lines with the camera placed at the same height distance and with the same lightening conditions.

Subjective Method

Subjective method was conducted by clients' self report.

The subjective method was conducted by questions that each client had to fill after every treatment, referring the immediate results they had noticed on each treated side, the notice of accumulative effect, the satisfaction of the patients from the results, sensation of the treatments etc.

The patients received satisfaction questionnaire which included yes/no questions and questions to be grade on 1 to 5 satisfaction scales (1—represents "Not At All" and 5 represents "Very Much").

Additionally there were open questions adapted to enable the patients the ability to express any kind of feeling following the treatments.

The following questionnaire was handed to the patients after each treatment (except of specific questions):

| Question | Score | Full Answer |
|---|---|---|
| Do you see any visual changes on the right side that was treated? Please describe in the "Full Answer" column. | Not at all   Very much<br>1   2  3  4   5 | |
| Are you satisfied from the visual changes on the right side that was treated? | Not at all   Very much<br>1   2  3  4   5 | |
| Is there any specific feeling you feel on the right side that was treated (tightness, lifting, stretched, fullness, swelled, loosen, ache, scratching)? Please describe in the "Full Answer" column. | Yes/No | |
| Are you satisfied from the feeling you feel on the right side that was treated? | Not at all   Very much<br>1   2  3  4   5 | |
| Do you see any visual changes on the left side that was treated? Please describe in the "Full Answer" column. | Not at all   Very much<br>1   2  3  4   5 | |

| Question | | Score | Full Answer |
|---|---|---|---|
| | Are you satisfied from the visual changes on the left side that was treated? | Not at all  Very much<br>1  2 3 4  5 | |
| | Is there any specific feeling you feel on the left side that was treated (tightness, lifting, stretched, fullness, swelled, loosen, ache, scratching)? Please describe in the "Full Answer" column. | Yes/No | |
| | Are you satisfied from the feeling you feel on the left side that was treated? | Not at all  Very much<br>1  2 3 4  5 | |
| Answer only from the second treatment | How long did the visual results last on the right side that was treated (Please describe in the "Full Answer" column)? | | |
| Answer only from the second treatment | How long did the visual results last on the left side that was treated (Please describe in the "Full Answer" column)? | | |
| Answer only after the 5$^{th}$ treatment | Do you feel that the results on the left side that was treated were accumulated from the first treatment? | Yes/No | |
| Answer only after the 5$^{th}$ treatment | Do you feel that the results on the right side that was treated were accumulated from the first treatment? | Yes/No | |
| Answer after the 8$^{th}$ treatment | Do you feel that the results on the left side that was treated were accumulated from the first treatment? | Yes/No | |
| Answer after the 8$^{th}$ treatment | Do you feel that the results on the right side that was treated were accumulated from the first treatment? | Yes/No | |
| General comments | | | |

Results

Study Group

All patients have shown immediate and highly noticeable results on both sides, after the first treatment; the skin tightness of the face and neck increased, it was smoother and with less wrinkles.

Further, after 5 treatments it was noticeable that the results were accumulated (based on comparison between pictures before the first treatment and pictures before the 5$^{th}$ treatment). After 8 treatments the skin tightness increased significantly. All clients indicated great satisfaction from the immediate visual results (tightness & stretched) as well as the long term results.

The average score of visual results and satisfaction on the right treated side was 4.66 (on 1 to 5 scale) and on the left treated side the average score was 4.8. 100% of the clients reported that the results on both sides remained all week along the sessions and were accumulated.

They report feeling of tightness, firm and highly comfort during the treatment in terms of the sensation ("Feels like hot stones massage") and expressed satisfaction from the sort time of the treatment.

Reference is now made to FIGS. 13A-13F which are pictures of one patient out of the study group treated with the device of the present invention. The pictures were taken before the treatment (see FIG. 13A for the forehead and FIG. 13B for the neck), after the first treatment (see FIG. 13C for the forehead and FIG. 13D for the neck) and after the 8$^{th}$ treatment (see FIG. 13E for the forehead and FIG. 13F for the neck).

First Control Group

All patients have shown immediate results on both sides, after the first treatment. However the results were more significant in terms of tightening and wrinkles fading on the right side compare to the left side.

The average score of visual results and satisfaction on the right treated side was 4.93 compare to the left treated side which was 4.8.

Following 5 treatment it was noticeable that the results were accumulated significantly on the right side in comparison to the results on the left side which lasted only for few days. 90% of the clients reported that the results on the right side remained all week along the first 5 treatments and were accumulated compare to 40% of the clients that reported maintenance of the results on the left side.

After 8 treatments the skin tightness increased even more on the right side and 100% of the clients reported accumulative results compare to the results of the left side which remained almost the same and only 50% of the clients reported maintenance of the results.

Both clients indicated higher satisfaction from the immediate and long term results on the right side compare to the left side. No difference between both treated sides in terms of comfort was expressed.

Reference is now made to FIGS. 14A-14F which are pictures of one patient out of the first control group treated with the device of the present invention on the right side and RF on the left side. The pictures were taken before the treatment (see FIG. 14A for the forehead and FIG. 14B for the neck), after the first treatment (see FIG. 14C for the forehead and FIG. 14D for the neck) and after the 8$^{th}$ treatment (see FIG. 14E for the forehead and FIG. 14F for the neck).

Second Control Group

All patients have shown immediate and very noticeable results (skin tightening and wrinkles fading) on the right side after the first treatment and the results have improved after the 5$^{th}$ and the 8$^{th}$ treatment.

The average score of visual results and satisfaction on the right treated side was 5.00 compare to the left treated side which was only 1.9.

It should be pointed out that on the left side they didn't show any results in terms of skin tightness along the treatments, although after the 4$^{th}$ treatment the skin showed some improvement (it looked more glowing and nourished).

All clients indicated high satisfaction from the immediate and long term results on the right side. 100% of the clients reported that the results on the right side remained all week along the first 5 treatments and were accumulated (and up to the 8$^{th}$ treatment) compare to 10% of the clients that reported maintenance of the results on the left side.

As for the left side, they reported after the 5$^{th}$ treatment satisfaction from the improved skin's condition and look, although they expressed some disappointment from not having results in terms of skin tightening. They reported high comfort in terms of the treatment sensation during the treatment of both sides.

Reference is now made to FIGS. 15A-15F which are pictures of one patient out of the second control group treated with the device of the present invention on the right side and PEMF on the left side. The pictures were taken before the treatment (see FIG. 15A for the forehead and FIG. 15B for the neck), after the first treatment (see FIG. 15C for the forehead and FIG. 15D for the neck) and after the 8$^{th}$ treatment (see FIG. 15E for the forehead and FIG. 15F for the neck).

Third Control Group

All patients have shown on the right side very noticeable immediate and accumulative results (skin tightening and wrinkles fading).

The satisfaction was very high.

On the left side visual results are seen; the immediate results were similar to the right side, however the accumulative results were less significant and noticeable compare with the left side.

The average score of visual results and satisfaction on the right treated side was 4.83 compare to the left treated side which was only 2.36.

90% of the clients reported that the results on the right side remained all week along the first 5 treatments (and up to the 8$^{th}$ treatment) and were accumulated.

Only 30% of the clients reported maintenance of the results on the left side. In term of satisfaction the clients expressed inconvenient due to the long duration of the treatment. Reference is now made to FIGS. 16A-16F which are pictures of one patient out of the third control group treated with the device of the present invention on the right side. The left side was treated with PEMF followed by RF. The pictures were taken before the treatment (see FIG. 16A for the forehead and FIG. 16B for the neck), after the first treatment (see FIG. 16C for the forehead and FIG. 16D for the neck) and after the 8$^{th}$ treatment (see FIG. 16E for the forehead and FIG. 16F for the neck).

The following tables (tables 3 and 4) summaries the results:

TABLE 3 average score (1 to 5 scale) of all participant in each group following all the treatments:

| Question | Study group | Control 1 | Control 2 | Control 3 |
|---|---|---|---|---|
| Do you see any visual changes on the right side that was treated? | 4.7 | 4.9 | 5 | 4.9 |
| Are you setisfied from the visual changes on the right side that was treated? | 4.7 | 5 | 5 | 4.8 |
| Are you setisfied from the feeling you feel on the right side that was treated? | 4.6 | 4.9 | 5 | 4.8 |
| Do you see any visual changes on the left side that was treated? | 4.9 | 2.5 | 1.9 | 2.4 |
| Are you setisfied from the visual changes on the left side that was treated? | 4.8 | 2.6 | 2 | 2.3 |
| Are you setisfied from the feeling you feel on the left side that was treated? | 4.7 | 2.4 | 1.8 | 2.4 |

TABLE 4 results of "Yes/No" Questions of all the patients in each group following all the treatments

| Question | Study group Yes | Study group No | Control 1 Yes | Control 1 No | Control 2 Yes | Control 2 No | Control 3 Yes | Control 3 No |
|---|---|---|---|---|---|---|---|---|
| Is there any specific feeling you feel on the right side that was treated? (tightness, lifting stretched, fullness, swelled, loosen, ache, scratching)? | 80% | 20% | 90% | 10% | 100% | 0% | 80% | 20% |
| Is there any specific feeling you feel on the left side that was treated? (tightness, lifting stretched, fullness, swelled, loosen, ache, scratching)? Answer only after the 5th treatment: | 90% | 10% | 60% | 40% | 40% | 60% | 50% | 50% |
| Do you feel that the results on the left side that was treated were accumulated from the first treatment? Answer only after the 5th treatment: | 100% | 0% | 40% | 60% | 10% | 90% | 30% | 70% |
| Do you feel that the results on the right side that was treated were accumulated from the first treatment? Answer only after the 8th treatment: | 100% | 0% | 90% | 10% | 100% | 0% | 90% | 10% |
| Do you feel that the results on the left side that was treated were accumulated from the first treatment? Answer only after the 8th treatment: | 100% | 0% | 50% | 50% | 20% | 80% | 30% | 70% |
| Do you feel that the results on the right side that was treated were accumulated from the first treatment? | 100% | 0% | 100% | 0% | 100% | 0% | 100% | 0% |

CONCLUSIONS

The synergetic effect of the device of the present invention clearly shows objectively and subjectively superior results when compare to the treatments in which only RF, or only PEMF were used.

It has shown that clients who were treated on the left side with PEMF technology had a much clearer difference between both sides. This is probably since they have not seen any tightness effect on the left side.

In addition it was shown that clients that were treated with the device of the present invention on both sides felt significant changes along the treatment. Yet more, it was harder for them to see the difference between both sides since both sides were treated with the device of the present invention and both sides had improved in the same way. 80%-100% out of all 40 participants answered "Yes" regarding questions concerning the tightness of the skin and the accumulative results on the right treated area. Only 10%-50% that were treated on the left side with other technology answered "Yes" regarding questions concerning the tightness of the skin and the accumulative results.

The results with the combined technology (the device provided by the present invention) were immediate and they maintained and improved from one treatment to the other. Immediate skin tightening has been seen due to the change of collagen fibers formation (they become shorter and thicker and as a result harder) induced by thermal technique of the RF.

Long lasting results has been seen due to the increase of new collagen fibers synthesis by using thermal (RF) and non-thermal (PEMF) technologies induced by the device of the present invention enables the formation change of greater amount of collagen fibers and as a results created physiological buttress that enabled better structural support of the skin.

The assets of the device of the present invention to the medical field are:

- Synergistic effect that stimulates dermal fibroblasts which produce new collagen, elastic and reticular fibers by using different mechanisms (Heating & non heating);
- Changing the form of a greater amount of collagen fiber by making them shorter and thicker; and,
- Angiogenesis—increasing the formation of new small blood vessels.

The invention claimed is:

1. A system (10) adapted to increase skin rejuvenation of a region of a patient's skin by synergistic application of heat and a pulsed electromagnetic field (PEMF) to a region of a patient's skin, said system comprising:
   a. a pulsed electromagnetic field generator for generating a pulsed electromagnetic field (PEMF) frequency (2) for providing electromagnetic pulses to said region of said patient's skin according to a predetermined protocol chosen from the group consisting of:
      i. a series of triangular shaped pulses with a frequency of 25 Hz and an intensity of 20 Gauss;
      ii. a series of square pulses of duration of about 5 ms and intensity of 12 Gauss, repeated at a frequency of 16 Hz;
      iii. a series of sets of pulses of duration of about 1 microsecond with a duty cycle of 50% with a pause of less than about 512 microseconds between each set of pulses; and,
      iv. any combination thereof;
   b. a deep tissue diathermy device (4) adapted to apply heat to said region of said patient's skin up to a temperature of 80 degrees Celsius; and
   c. an electromagnetic pulse regulator (6) adapted to regulate said electromagnetic pulses, said control system comprising:
      i. processing parameter storage means for storing in a communicable database predetermined parameters defining (i) safe treatment parameters and (ii) unsafe treatment parameters; said communicable database predetermined parameters are selected from the group consisting of time of said treatment, temperature of said tissue, ratio of said time/said temperature, Frequency, power, energy applied by the pulses of said pulsed electromagnetic frequency generator, depth of said treated tissue, magnetic field intensity, tissue impedance, specific absorption rate (SAR), treatment depth, superficial muscle contractions or a combination thereof;
      ii. electromagnetic and heat radiation sensing means for sensing electromagnetic radiation and heat radiation parameters selected from the group consisting of a time of said treatment, temperature of said tissue, ratio of said time/said temperature, Frequency, power, Intensity of said ultrasound irradiation, energy applied by the pulses of said pulsed electromagnetic frequency generator, depth of said treated tissue, magnetic field intensity, tissue impedance, specific absorption rate (SAR), treatment depth, superficial muscle contractions or a combination thereof; and
      iii. regulating electromagnetic and heat radiation regulation means for allowing said electromagnetic radiation and heat radiation if said electromagnetic radiation and heat radiation parameters are within said safe treatment parameters and to stop the electromagnetic radiation if the radiation parameters are in said unsafe treatment parameters;
   wherein said system is adapted to provide skin rejuvenation via a synergistic combination of PEMF and deep tissue diathermy,
   wherein said system further comprises at least two electrodes (41) adapted to be placed on said region of a patient's skin, each of said electrodes being encircled by at least one helical coil (42),
   wherein each of said electrodes is adapted for both (i) providing electromagnetic pulses to said region of said patient's skin; and, (ii) applying heat up to temperature 80 degrees Celsius to said region of a patient's skin, and
   wherein all of said electrodes are adapted to simultaneously provide said electromagnetic pulses to said region of said patient's skin and apply heat to said region of said patient's skin.

2. The system according to claim 1, wherein said deep tissue diathermy device (4) is selected from any device emitting RF radiation or an electrical current producing means adapted for producing electrical current absorbed by subcutaneous tissue, ultrasonic diathermy, an optical device, electromagnetic induction, sound waves emitting instrument and direct heat applying instrument.

3. The system according to claim 1, wherein said deep tissue diathermy device (4) additionally comprises:
   a. at least one electrical output device adapted to generate either RF electromagnetic energy or electrical current; and
   b. at least two electrodes electrically coupled to said electrical output device and placed on said skin region, wherein all said electrodes are adapted to simultaneously apply said RF energy or said electrical current to said skin region.

4. The system according to claim 1, wherein said pulsed electromagnetic frequency generator is adapted to provide a dynamic magnetic field such that said electromagnetic pulses vary with time.

5. The system according to claim 1, wherein at least one condition is being held true (a) the shape of said electromagnetic pulse is selected from the group consisting of square wave, a sine wave, a triangular wave, sawtooth wave, ramp waves, spiked wave or any combination thereof; (b) the magnetic field intensity of each pulse applied by said pulsed electromagnetic frequency generator (2) ranges between about 0 and about 3 Tesla; (c) the duration of each pulse applied by said pulsed electromagnetic frequency generator (2) ranges between about 3 and about 1000 milliseconds; (d) the frequency applied by the pulses of said pulsed electromagnetic frequency generator (2) ranges between about 1 Hz and about 1 MHz; (e) the energy applied by the pulses of said pulsed electromagnetic frequency generator (2) ranges between about 1 and about 150 watts per pulse or any combination thereof.

6. The system according to claim 1, wherein at least one condition is being held true an optical device is adapted to emit light in wavelengths absorbed by subcutaneous tissue such that said subcutaneous tissue is heated; a sound waves emitting instrument is adapted to emit sound waves absorbed by the subcutaneous tissue such that said subcutaneous tissue is heated.

7. The system according to claim 1, wherein said temperature is higher than about 30 and lower than about 80 degrees Celsius.

8. The system according to claim 1, wherein a power supply and control system (6) includes a skin cooling means for cooling the skin.

9. The system according to claim 1, wherein said system (10) is encased in at least one platform.

10. The system according to claim 1, wherein said pulsed electromagnetic frequency generator (2) and said deep tissue diathermy device (4) have more than one applicator to treat more than one body part simultaneously; further wherein said pulsed electromagnetic frequency generator (2) has electrostatic shielding.

11. The system according to claim 1, wherein said system is adapted to operate according to an IEC protocol selected from the group consisting of IEC 60601-2-33, IEC 60601-2-5, IEC 60601-2-3, IEC 60601-1-8, IEC 60601-1-6, IEC 60601-1-4, IEC 60601-1-2, IEC 60601-1-1, and any combination thereof.

* * * * *